US011279980B2

(12) United States Patent
Delker et al.

(10) Patent No.: US 11,279,980 B2
(45) Date of Patent: Mar. 22, 2022

(54) METHODS AND COMPOSITIONS FOR PREDICTING A COLON CANCER SUBTYPE

(71) Applicant: UNIVERSITY OF UTAH RESEARCH FOUNDATION, Salt Lake City, UT (US)

(72) Inventors: Don Delker, West Valley City, UT (US); Priyanka Kanth, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 0 days.

(21) Appl. No.: 16/072,162

(22) PCT Filed: Jan. 24, 2017

(86) PCT No.: PCT/US2017/014727
§ 371 (c)(1),
(2) Date: Jul. 23, 2018

(87) PCT Pub. No.: WO2017/132139
PCT Pub. Date: Aug. 3, 2017

(65) Prior Publication Data
US 2019/0032147 A1 Jan. 31, 2019

Related U.S. Application Data

(60) Provisional application No. 62/286,821, filed on Jan. 25, 2016, provisional application No. 62/303,133, filed on Mar. 3, 2016.

(51) Int. Cl.
*C12Q 1/6886* (2018.01)
*C12Q 1/6806* (2018.01)
*C12Q 1/686* (2018.01)

(52) U.S. Cl.
CPC ......... *C12Q 1/6886* (2013.01); *C12Q 1/6806* (2013.01); *C12Q 1/686* (2013.01); *C12Q 2600/112* (2013.01); *C12Q 2600/118* (2013.01); *C12Q 2600/154* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| 6,248,526 | B1 * | 6/2001 | Weimer ............... | C12Q 1/6846 435/6.11 |
|---|---|---|---|---|
| 2012/0225425 | A1 | 9/2012 | Navari et al. | |
| 2013/0332083 | A1 * | 12/2013 | Van Laar ............. | C12Q 1/6886 702/19 |
| 2015/0275307 | A1 | 10/2015 | Hagedorn et al. | |
| 2015/0320779 | A1 | 11/2015 | Fillmore et al. | |

FOREIGN PATENT DOCUMENTS

WO WO-2012/087983 A1 6/2012

OTHER PUBLICATIONS

Affymetrix (U133, www.affymetrix.com downloaded Feb. 14, 2021) (Year: 2021).*
Abe, M. et al., Identification of genes targeted by CpG island methylator phenotype in neuroblastomas, and their possible integrative involvement in poor prognosis. Oncology. 2008; 74(1-2):50-60.
Anders, S. and Huber, W., Differential expression analysis for sequence count data. Genome Biol. 2010; 11(10):R106 (12 pages).
Andersen, C.L. et al., Normalization of Real-Time Quantitative Reverse Transcription-PCR Data: A Model-Based Variance Estimation Approach to Identify Genes Suited for Normalization, Applied to Bladder and Colon Cancer Data Sets. Cancer Res. 2004; 64(15):5245-50.
Benjamini, Y. and Hochberg, Y., Controlling the false discovery rate: a practical and powerful approach to multiple testing. J Roy Statist Soc Ser B (Methodological). 1995; 57(1):289-300.
Boparai, K.S. et al., Increased colorectal cancer risk during follow-up in patients with hyperplastic polyposis syndrome: a multicentre cohort study. Gut. 2010; 59(8):1094-100.
Burgess, N.G. et al., Clinical and endoscopic predictors of cytological dysplasia or cancer in a prospective multicentre study of large sessile serrated adenomas/polyps. Gut. 2016; 65(3):437-46.
Burnett-Hartman, A.N. et al., Genomic aberrations occurring in subsets of serrated colorectal lesions but not conventional adenomas. Cancer Res. 2013; 73(9):2863-72 (18 pages).
Caruso, M. et al., Claudin-1 Expression Is Elevated in Colorectal Cancer Precursor Lesions Harboring the BRAF V600E Mutation. Transl Oncol. 2014; 7(4):456-63.
Caruso, M. et al., Over-expression of cathepsin E and trefoil factor 1 in sessile serrated adenomas of the colorectum identified by gene expression analysis. Virchows Arch. 2009; 454(3):291-302.
Cerami, E. et al., The cBio cancer genomics portal: an open platform for exploring multidimensional cancer genomics data. Cancer Discov. 2012; 2(5):401-4 (7 pages).

(Continued)

*Primary Examiner* — Katherine D Salmon
(74) *Attorney, Agent, or Firm* — Ballard Spahr LLP

(57) ABSTRACT

Disclosed herein are methods for identifying a genetic susceptibility to colon cancer in as subject, the method comprising determining the mRNA expression level of one or more of FSCN1, ZIC2, ZIC5, CRYBA2, MUC6, TRNP1 and SEMG1 in a colon tissue sample in the subject, where a ratio of the sample expression level of one or more genes in the panel to a reference expression level of one or more genes in the panel indicates cancer or and increased susceptibility of cancer. Disclosed herein are diagnostic devices comprising one or more biomarkers, wherein the biomarkers are FSCN1, ZIC2, ZIC5, CRYBA2, MUC6, TRNP1 and SEMG1; and a gene expression panel consisting of primers or probes for detecting FSCN1, ZIC2, ZIC5, CRYBA2, MUC6, TRNP1 and SEMG1 in a sample, and methods for assessing risk of developing colon cancer in a subject.

2 Claims, 26 Drawing Sheets

(56) References Cited

OTHER PUBLICATIONS

Chan, D.W. et al., Zic2 synergistically enhances Hedgehog signalling through nuclear retention of Gli1 in cervical cancer cells. J Pathol. 2011; 225(4):525-34.
Chen, L.C. et al., Alteration of gene expression in normal-appearing colon mucosa of APCmin mice and human cancer patients. Cancer Res. 2004; 64(10):3694-700.
Ciriello, G. et al., Mutual exclusivity analysis identifies oncogenic network modules. Genome Res. 2012; 22(2):398-406.
Conesa-Zamora, P. et al., Expression profiling shows differential molecular pathways and provides potential new diagnostic biomarkers for colorectal serrated adenocarcinoma. Int J Cancer. 2013; 132(2):297-307.
Damania, D. et al., Nanocytology of rectal colonocytes to assess risk of colon cancer based on field cancerization. Cancer Res. 2012; 72(11):2720-7 (18 pages).
De Sousa, E.M. et al., Poor-prognosis colon cancer is defined by a molecularly distinct subtype and develops from serrated precursor lesions. Nat Med. 2013; 19(5):614-8.
Delker, D.A. et al., RNA Sequencing of Sessile Serrated Colon Polyps Identifies Differentially Expressed Genes and Immunohistochemical Markers. PLoS One. 2014; 9(2):1-12.
Disario, J.A. et al., Prevalence and malignant potential of colorectal polyps in asymptomatic, average-risk men. Am J Gastroenterol. 1991; 86(8):941-5.
Donehower, L.A. et al., MLH1-silenced and non-silenced subgroups of hypermutated colorectal carcinomas have distinct mutational landscapes. J Pathol. 2013; 229(1):99-110 (19 pages).
Folkers, M.E. et al., ENCODE tiling array analysis identifies differentially expressed annotated and novel 5' capped RNAs in hepatitis C infected liver. PLoS One. 2011; 6(2):e14697 (14 pages).
Gao, J. et al., Integrative analysis of complex cancer genomics and clinical profiles using the cBioPortal. Sci Signal. 2013; 6(269):pl1 (34 pages).
Gonzalo, D.H. et al., Gene expression profiling of serrated polyps identifies annexin A10 as a marker of a sessile serrated adenoma/polyp. J Pathol. 2013; 230(4):420-9.
Guarinos, C. et al., Clinical subtypes and molecular characteristics of serrated polyposis syndrome. Clin Gastroenterol Hepatol. 2013; 11(6):705-11.
Guinney, J. et al., The consensus molecular subtypes of colorectal cancer. Nat Med. 2015; 21(11):1350-6 (33 pages).
Hawthorn, L. et al., Evidence for field effect cancerization in colorectal cancer. Genomics. 2014; 103(2-3):211-21.
Holme, Ø. et al., Long-term risk of colorectal cancer in individuals with serrated polyps. Gut. 2015; 64(6):929-36.
Huang, C.S. et al., The clinical significance of serrated polyps. Am J Gastroenterol. 2011; 106(2):229-40.
Lino, H. et al., DNA microsatellite instability in hyperplastic polyps, serrated adenomas, and mixed polyps: a mild mutator pathway for colorectal cancer? J Clin Pathol. 1999; 52(1):5-9.
Jasperson, K.W. et al., Serrated polyposis: colonic phenotype, extracolonic features, and familial risk in a large cohort. Dis Colon Rectum. 2013; 56(11):1211-6 (12 pages).
Kahi, C.J. et al., Prevalence and variable detection of proximal colon serrated polyps during screening colonoscopy. Clin Gastroenterol Hepatol. 2011; 9(1):42-6.
Kang, S.K. et al., Role of human aquaporin 5 in colorectal carcinogenesis. Am J Pathol. 2008; 173(2):518-25.
Khalid, O. et al., Reinterpretation of histology of proximal colon polyps called hyperplastic in 2001. World J Gastroenterol. 2009; 15(30):3767-70.
Lieberman, D.A. et al., Use of colonoscopy to screen asymptomatic adults for colorectal cancer. N Engl J Med. 2000; 343(3):162-8.
Lieberman, D.A. et al., United States Multi-Society Task Force on Colorectal Cancer. Guidelines for colonoscopy surveillance after screening and polypectomy: a consensus update by the US Multi-Society Task Force on Colorectal Cancer. Gastroenterology. 2012; 143(3): 844-57.
Lochhead, P. et al., Etiologic field effect: reappraisal of the field effect concept in cancer predisposition and progression. Mod Pathol. 2015; 28(1):14-29 (28 pages).
Love, M.I. et al., Moderated estimation of fold change and 20 dispersion for RNA-Seq data with DESeq2. Gen Biol. 2014; 15(12):550 (21 pages).
Luo, Y. et al., Field cancerization in the colon: a role for aberrant DNA methylation? Gastroenterol Rep (Oxf). 2014; 2(1):16-20.
Ma, Y. and Machesky, L.M., Fascin1 in carcinomas: Its regulation and prognostic value. Int J Cancer. 2015; 137(11):2534-44.
Mäkinen, M.J., Colorectal serrated adenocarcinoma. Histopathology. 2007; 50(1):131-50.
Marchini, S. et al., The zinc finger gene ZIC2 has features of an oncogene and its overexpression correlates strongly with the clinical course of epithelial ovarian cancer. Clin Cancer Res. 2012; 18(16):4313-24 (24 pages).
Merzdorf, C.S., Emerging roles for zic genes in early development. Dev Dyn. 2007; 236(4):922-40.
Neuhaus, J. et al., Seminal plasma as a source of prostate cancer peptide biomarker candidates for detection of indolent and advanced disease. PLoS One. 2013; 8(6):e67514 (13 pages).
Nix, D.A. et al., Empirical methods for controlling false positives and estimating confidence in ChIP-Seq peaks. BMC Bioinformatics. 2008; 9:523 (9 pages).
O'Brien, M.J., Hyperplastic and serrated polyps of the colorectum. Gastroenterol Clin North Am. 2007; 36(4):947-68.
O'Brien, M.J. et al., Colorectal serrated pathway cancers and precursors. Histopathology. 2015; 66(1):49-65.
Owens, S.R. et al., Selective expression of gastric mucin MUC6 in colonic sessile serrated adenoma but not in hyperplastic polyp aids in morphological diagnosis of serrated polyps. Mod Pathol. 2008; 21(6):660-9.
Papic, N. et al., RNA-sequencing analysis of 5' capped RNAs identifies many new differentially expressed genes in acute hepatitis C virus infection. Viruses. 2012; 4(4):581-612.
Paz, M.F. et al., Genetic unmasking of epigenetically silenced tumor suppressor genes in colon cancer cells deficient in DNA methyltransferases. Hum Mol Genet. 2003; 12(17):2209-19.
Popovici, V. et al., Identification of a poor-prognosis BRAF-mutant-like population of patients with colon cancer. J Clin Oncol. 2012; 30(12):1288-95.
Rashid, A. et al., Phenotypic and molecular characteristics of hyperplastic polyposis. Gastroenterology. 2000; 119(2):323-32.
Richter, J.M. et al., Genetic mechanisms in interval colon cancers. Dig Dis Sci. 2 014; 59(9):2255-63.
Samadder, N.J. et al. Characteristics of missed or interval colorectal cancer and patient survival: a population-based study. Gastroenterology. 2014; 146(4):950-60.
Samowitz, W.S. et al., Evaluation of a large, population-based sample supports a CpG island methylator phenotype in colon cancer. Gastroenterology. 2005; 129(3):837-45.
Sanek, N.A. et al., Zebrafish zic2a patterns the forebrain through modulation of Hedgehog-activated gene expression. Development. 2009; 136(22):3791-800 (26 pages).
Snover, D.C. et al., Serrated Polyps of the colon and rectum and serrated polyposis. Boxman, F T, Hruban, R H, Theise, N D, ed WHO Classification of Tumors of the Digestive System IARC, Lyon, 2010; 160-5.
Stahl, R.I. et al., Trnp1 regulates expansion and folding of the mammalian cerebral cortex by control of radial glial fate. Cell. 2013; 153(3):535-49.
Sun, Y. et al., MIR-429 inhibits cells growth and invasion and regulates EMT-related marker genes by targeting Onecut2 in colorectal carcinoma. Mol Cell Biochem. 2014; 390(1-2):19-30.
The Cancer Genome Atlas Network. Comprehensive molecular characterization of human colon and rectal cancer. Nature. 2012; 487(7407):330-7 (22 pages).
Torlakovic, E. et al., Morphologic reappraisal of serrated colorectal polyps. Am J Surg Pathol. 2003; 27(1):65-81.
Walsh, M.D.et al., Expression of MUC2, Mucsac, MUC5B, and MUC6 mucins in colorectal cancers and their association with the CpG island methylator phenotype. Mod Pathol. 2013; 26(12):1642-56.

(56) References Cited

OTHER PUBLICATIONS

Weston, A.P. and Campbell, D.R., Diminutive colonic polyps: histopathology, spatial distribution, concomitant significant lesions, and treatment complications. Am J Gastroenterol. 1995; 90(1):24-8.
Wong, N.A.C.S. et al., Observer agreement in the diagnosis of serrated polyps of the large bowel. Histopathology. 2009; 55(1):63-6.
International Search Report and Written Opinion dated Apr. 10, 2017 by the International Searching Authority for Patent Application No. PCT/US2017/014727, which was filed on Jan. 24, 2017 and published as WO 2017/132139 on Aug. 3, 2017 (Inventor—Delker et al.; Applicant—University of Utah Research Foundation) (10 pages).
International Preliminary Reporton Patentability dated Jul. 31, 2018 by the International Searching Authority for Patent Application No. PCT/US2017/014727, which was filed on Jan. 24, 2017 and published as WO 2017/132139 on Aug. 3, 2017 (Inventor—Delker et al.; Applicant—University of Utah Research Foundation) (8 pages).
U.S. Appl. No. 62/286,821, filed Jan. 25, 2016, Don Delker (Univ. of Utah Res. Found.).
U.S. Appl. No. 62/303,133, filed Mar. 3, 2016, Don Delker (Univ. of Utah Res. Found.).
PCT/US2017/014727 (WO 2017/132139), filed Jan. 24, 2017 (Aug. 3, 2017), Don Delker (Univ. of Utah Res. Found.).

\* cited by examiner

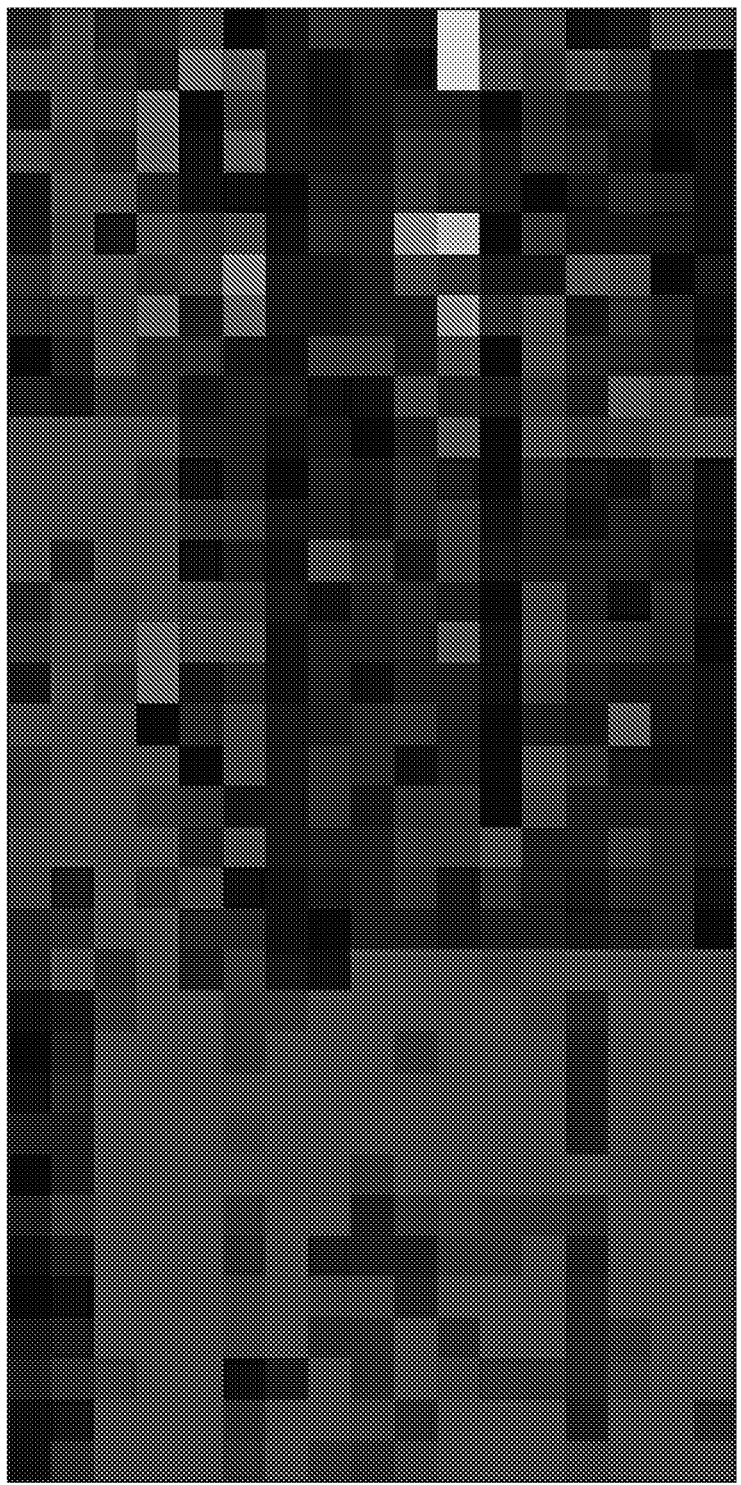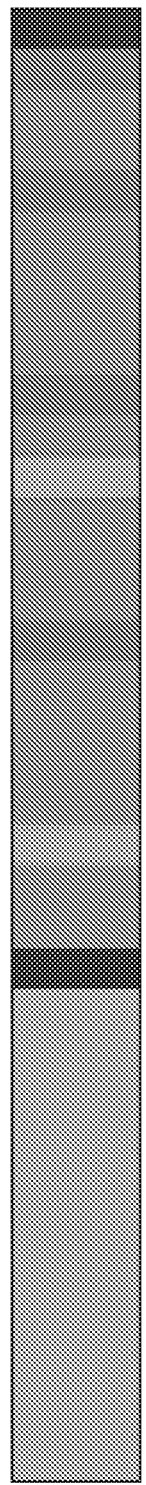
FIG. 4A continued

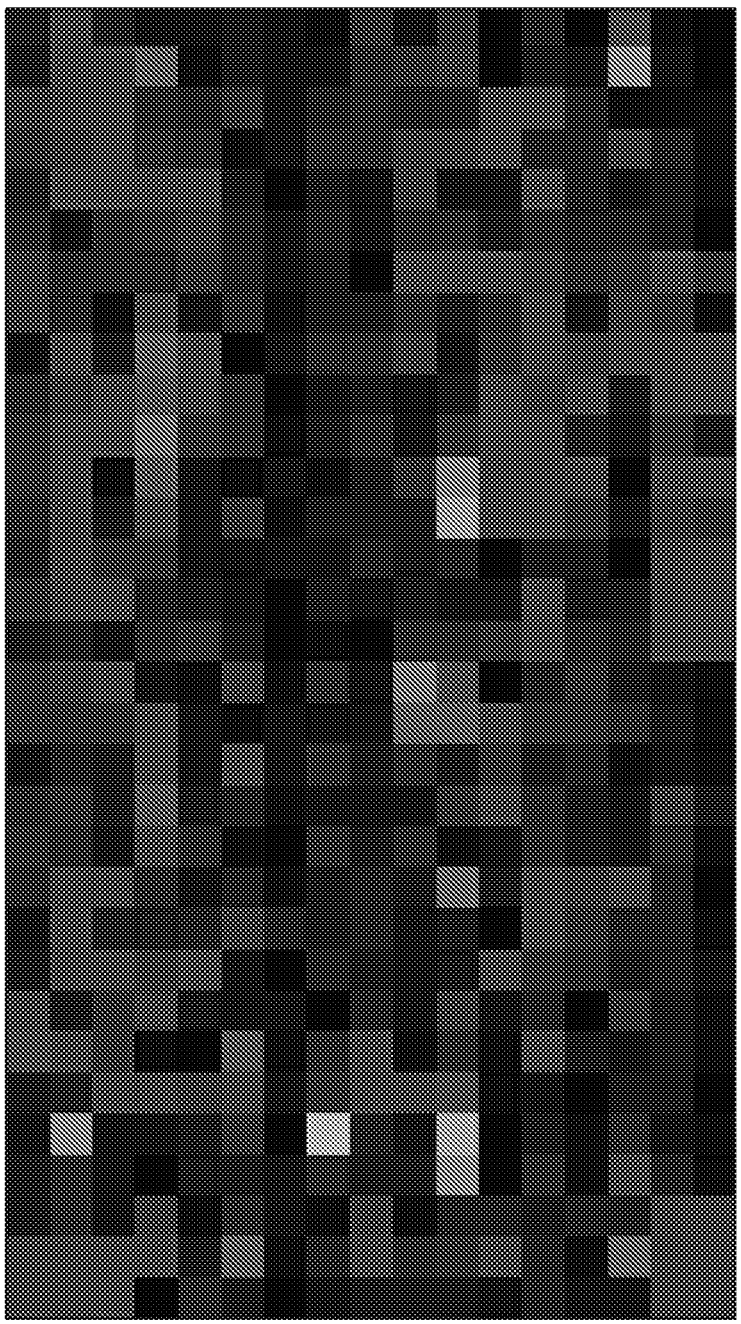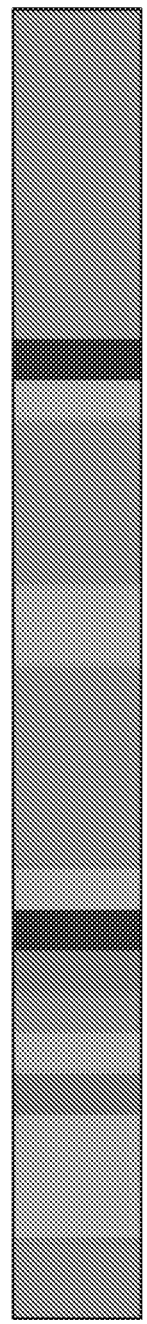
FIG. 4A continued

Frequency of Increased mRNA Expression in SSA/P Signatures Genes in 30 Hypermutated and 165 Non-Hypermutated Colon Cancers from the Cancer Genome Atlas

| Gene Symbol | Gene Description | Hypermutated CC Incidence (%) | Non-Hypermutated CC Incidence (%) | Fisher Exact P-value |
|---|---|---|---|---|
| FSCN1 | Fascin actin-binding protein 1 | 9 (30) | 3 (2) | <0.001 |
| ZIC5 | Zic family member 5 | 7 (23) | 5 (3) | <0.001 |
| CRYBA2 | Crystallin, beta A2 | 5 (17) | 0 (0) | <0.001 |
| SEMG1 | Semenogelin | 4 (13) | 0 (0) | <0.001 |
| ZIC2 | Zic family member 2 | 6 (20) | 4 (2) | 0.001 |
| TRNP1 | TMF1-regulated nuclear protein 1 | 6 (20) | 5 (3) | 0.002 |
| MUC6 | Mucin 6 | 4 (13) | 1 (1) | 0.002 |
| FOSL1 | FOS-like antigen 1 | 3 (10) | 1 (1) | 0.012 |
| ALDH1L1 | Aldehyde dehydrogenase 1 family member L1 | 5 (17) | 7 (4) | 0.022 |
| KLK10 | Kallikrein related peptidase 10 | 3 (10) | 4 (2) | 0.075 |
| SLC18A1 | Solute carrier family 18, member 1 | 3 (10) | 4 (2) | 0.075 |
| VNN1 | Vanin 1 | 3 (10) | 4 (2) | 0.075 |
| MUC17 | Mucin 17 | 3 (10) | 13 (8) | 0.717 |
| ANXA10 | Annexin A10 | 1 (3) | 2 (1) | 0.396 |
| CLDN1 | Claudin 1 | 1 (3) | 11 (7) | 0.696 |

FIG. 9

Individual Genes

| Gene | Sensitivity | Specificity |
|---|---|---|
| ZIC5 | 0.677 | 0.887 |
| ZIC2 | 0.548 | 0.854 |
| FSCN1 | 0.516 | 0.947 |
| SEMG1 | 0.484 | 0.960 |
| TRNP1 | 0.484 | 0.947 |
| CRYBA2 | 0.419 | 0.960 |
| MUC6 | 0.258 | 0.987 |
| ANXA10 | 0.194 | 0.974 |
| CLDN1 | 0.065 | 0.881 |

FIG. 10A

Seven Gene Panel

| Minimum # Genes Positive | Sensitivity | Specificity |
|---|---|---|
| 1 | 0.935 | 0.722 |
| 2 | 0.839 | 0.874 |
| 3 | 0.613 | 0.960 |
| 4 | 0.419 | 0.987 |
| 5 | 0.290 | 1.000 |
| 6 | 0.194 | 1.000 |
| 7 | 0.097 | 1.000 |

FIG. 10B

Frequency of Increased Expression in SSA/P Signature Genes in 29 CIMP-H and/or MLH1 Silenced and 166 not CIMP-H or MLH1 Silenced Colon Cancers from the Cancer Genome Atlas

| Gene Symbol | Gene Description | CIMP-H and/or MLH1 Silenced CC Incidence (%) | Not CIMP-H or MLH1 Silenced CC Incidence (%) | Fisher Exact P-value |
|---|---|---|---|---|
| FSCN1 | Fascin actin-binding protein 1 | 9 (31) | 3 (2) | <0.001 |
| ZIC5 | Zic family member 5 | 8 (28) | 4 (2) | <0.001 |
| KLK10 | Kallikrein related peptidase 10 | 5 (17) | 2 (1) | <0.001 |
| FOSL1 | FOS-like antigen 1 | 4 (14) | 0 (0) | <0.001 |
| SEMG1 | Semenogelin | 4 (14) | 0 (0) | <0.001 |
| TRNP1 | TMF1-regulated nuclear protein 1 | 6 (21) | 5 (3) | 0.002 |
| CRYBA2 | Crystallin, beta A2 | 4 (14) | 1 (1) | 0.002 |
| MUC6 | Mucin 6 | 4 (14) | 1 (1) | 0.002 |
| SULT1C2 | Sulfotransferase family 1C member 2 | 4 (14) | 1 (1) | 0.002 |
| FEZF1 | Forebrain embryonic zinc finger 1 | 5 (17) | 6 (4) | 0.013 |
| ZIC2 | Zic family member 2 | 4 (14) | 4 (2) | 0.018 |
| SLC18A1 | Solute carrier family 18, member 1 | 3 (10) | 4 (2) | 0.069 |
| ALDH1L1 | Aldehyde dehydrogenase 1 family member L1 | 4 (14) | 8 (5) | 0.083 |
| MUC17 | Mucin 17 | 4 (14) | 11 (7) | 0.247 |
| DCDC2 | Doublecortin domain containing 2 | 3 (10) | 9 (5) | 0.392 |
| ANXA10 | Annexin A 10 | 0 (0) | 3 (2) | 1.000 |
| CLDN1 | Claudin 1 | 1 (3) | 11 (7) | 1.000 |

FIG. 11

Co-Occurrence and Mutual Exclusivity Analysis of SSA/P Signature Genes with Alterations in *BRAF*

| Gene A | Gene B | p-value | Log Odds Ratio | Association |
|---|---|---|---|---|
| SEMG1 | BRAF | <0.001 | >3.00 | Significant co-occurrence |
| MUC6 | BRAF | <0.001 | >3.00 | Significant co-occurrence |
| FSCN1 | BRAF | <0.001 | 2.91 | Significant co-occurrence |
| TRNP1 | BRAF | <0.001 | 2.29 | Significant co-occurrence |
| ZIC5 | BRAF | <0.001 | 2.49 | Significant co-occurrence |
| AQP5 | BRAF | 0.002 | >3.00 | Significant co-occurrence |
| PI3 | BRAF | 0.002 | >3.00 | Significant co-occurrence |
| SLC18A1 | BRAF | 0.005 | 2.06 | Significant co-occurrence |
| NTRK3 | BRAF | 0.012 | 2.02 | Significant co-occurrence |
| CRYBA2 | BRAF | 0.018 | 2.39 | Significant co-occurrence |
| MUC17 | BRAF | 0.021 | 1.14 | Significant co-occurrence |
| DPCR1 | BRAF | 0.032 | 1.98 | Significant co-occurrence |
| SCGN | BRAF | 0.043 | 1.44 | Significant co-occurrence |
| ANXA10 | BRAF | 0.0514 | 1.68 | Tendency towards co-occurrence |
| CLDN1 | BRAF | 0.5059 | -0.55 | Tendency towards mutual exclusivity |

FIG. 12

Seven Gene Panel + *ANXA10*

| Minimum # Genes Positive | Sensitivity | Specificity |
|---|---|---|
| 1 | 0.968 | 0.715 |
| 2 | 0.839 | 0.868 |
| 3 | 0.613 | 0.954 |
| 4 | 0.419 | 0.980 |
| 5 | 0.323 | 1.000 |
| 6 | 0.258 | 1.000 |
| 7 | 0.161 | 1.000 |

FIG. 13A

Seven Gene Panel + *CLEN1*

| Minimum # Genes Positive | Sensitivity | Specificity |
|---|---|---|
| 1 | 0.935 | 0.629 |
| 2 | 0.839 | 0.854 |
| 3 | 0.613 | 0.954 |
| 4 | 0.452 | 0.987 |
| 5 | 0.323 | 1.000 |
| 6 | 0.194 | 1.000 |
| 7 | 0.097 | 1.000 |

FIG. 13B

METHODS AND COMPOSITIONS FOR PREDICTING A COLON CANCER SUBTYPE

CROSS REFERENCE TO RELATED APPLICATIONS

This application claims the benefit of priority under 35 U.S.C. § 371 of International Application No. PCT/US2017/014727, filed on Jan. 24, 2017, which claims the benefit of the filing date of U.S. Provisional Applications 62/286,821, which was filed on Jan. 25, 2016, and 62/303,133, which was filed on Mar. 3, 2016. The content of these earlier filed applications is hereby incorporated by reference herein in its entirety.

STATEMENT REGARDING FEDERALLY FUNDED RESEARCH

This invention was made with government support under grant numbers CA176130, CA148068, CA073992, CA146329, CA042014 and TR001067 awarded by the National Institutes of Health. The government has certain rights in the invention.

FIELD OF THE INVENTION

The present disclosure relates to methods of determining the susceptibility of a subtype of colon cancer, and in particular in sessile serrated adenomas/polys and methods for diagnosing a subtype of colon cancer in an individual.

BACKGROUND

Colon cancer is the second leading cause of cancer-related deaths in United States and third most common cancer in men and women (1). Serrated colon polyps are found in 12-36% of patients undergoing routine screening colonoscopy (2-4). Serrated polyps are classified into three groups: hyperplastic polyps (HPs), sessile serrated adenoma/polyps (SSA/Ps), and traditional serrated adenomas (TSAs) (5). Both SSA/Ps and relatively rare TSAs have malignant potential. Histologically, SSA/Ps often has basilar crypt dilation, which can present as an L-shaped or inverted T-shaped morphology. HPs lack these specific features (6). Differentiating SSA/Ps, however, from HPs by colonoscopy or histopathology remains difficult due to overlapping morphological and pathological features (7, 8). Limited information on gene expression profiles differentiating SSA/Ps from traditional hyperplastic polyps is available.

BRIEF DESCRIPTION OF THE DRAWINGS

FIG. 1A shows differentially expressed genes with a ≥2-fold change and FDR<0.05 in SSA/Ps (n=12 for syndromic and n=9 for sporadic) compared to control right colon (n=10) and HPs (n=10) compared to control left colon (n=10). FIG. 1B shows the relative abundance of protein coding and non-coding RNAs differentially expressed in SSA/Ps. Non-coding RNAs included antisense non-coding RNAs, long intergenic non-coding RNAs (lincRNAs), pseudogenes and other miscellaneous RNAs including immunoglobulin and intronic RNAs.

FIG. 2A shows genes with ≥4-fold change and FDR<0.05 in syndromic SSA/Ps (n=12), sporadic SSA/Ps (n=9) and HPs (n=10). Syndromic and sporadic SSA/Ps were compared to control right colon and HPs to control left colon. FIG. 2B shows relative expression of 27 protein-coding genes in syndromic SSA/Ps, sporadic SSA/Ps, HPs and control left and right colon. $Log_2$ ratios comparing each individual sample to the mean of all samples were used for hierarchical clustering. Two right-sided HPs are labeled in red, and five left-sided SSA/Ps are labeled in green. FIG. 2C shows mean fold change expression of the same 27 protein coding genes described in FIG. 2B in normal colon, adenomas, HPs and sporadic and syndromic SSA/Ps.

FIG. 3A shows the principal component analysis of $log_2$ ratios for each individual serrated polyp compared to the mean of all serrated polyps. Principal component 1 (PC1) accounted for 28% of the variation in the data and separated most SSA/Ps (red) from HPs (blue). Twenty-eight of thirty-one serrated polyps (~90%) clustered correctly and similar to the nominal error rate found in the cross validation results. FIG. 3B shows the relative expression (log of normalized reads (RPKM) of the same 28 genes described in FIG. 3A in SSA/Ps and HPs. Six genes (circles) were overexpressed in SSA/Ps compared to HPs (range 2.8 to 3.7 fold) and 22 genes (squares) were underexpressed in SSA/Ps compared to HPs (range −2.2 to −6.7).

FIG. 4A shows $Log_2$ ratios comparing individual colon cancers (n=72) and SSA/Ps (n=21) to the mean of 14 uninvolved and 10 control colon samples (n=24) were used for hierarchical clustering. "Tissue" color bar shows colon adenocarcinomas (orange) and SSA/Ps (yellow). "MSI status" color bar shows microsatellite stable (MSS) cancers (dark blue), MSI-H cancers (red) and MSI-L cancers (light orange). SSA/Ps and colon cancers not evaluated for MSI (light blue). FIG. 4B shows the percentage of TCGA colon cancers showing overexpression of FSCN1, ZIC2, ZIC5, CRYBA2, MUC6, TRNP1 and/or SEMG1 shown in FIG. 9.

FIG. 9 is a table showing the frequency of increased mRNA expression in SSA/P signatures genes in hypermutated and non-hypermutated colon cancers from the Cancer Genome Atlas (TCGA). The Table lists 13/51 signature genes that show frequent (≥10%) increased mRNA expression in hypermutated colon cancers. Incidence of increased mRNA expression is also shown for two previously developed SSA/P gene markers, annexin A10 (ANXA10) and claudin 1 (CLDN1).

FIG. 10A-B depicts the sensitivity and specificity of a seven gene panel in identifying BRAF mutant, CIMP-H and/or MLH1 silenced colon cancers from the Cancer Genome Atlas (TCGA). FIG. 10A shows the sensitivity and specificity of each of a seven gene panel, and two previously described SSA/P gene markers (ANXA10, CLDN1), in identifying BRAF mutant, CIMP-H and/or MLH1 silenced colon cancers. FIG. 10B shows the sensitivity and specificity of one or more genes from a seven gene panel showing a ≥2-fold increased expression in serrated pathway cancers compared to the average of all colon cancers.

FIG. 11 is a table showing the frequency of increased mRNA expression in SSA/P signature genes in CIMP-H and/or MLH1 silenced colon cancers (CC) from the Cancer Genome Atlas (TCGA).

FIG. 12 is a table showing the results of the co-occurrence and mutual exclusivity analysis of SSA/P signature genes with alterations in BRAF. FIG. 12 shows mutually exclusive and concurrent DNA and mRNA changes (somatic mutations and mRNA expression) with alterations in BRAF in 195 TCGA colon cancers available in the cBioPortal for Cancer Genomics.

FIG. 13A-B shows the cross-validated sensitivity and specificity of SSA/P geven gene panel and ANXA10 or CLDN1. FIG. 13A shows the sensitivity and specificity of each of a seven gene panel plus ANXA10 in identifying BRAF mutant, CIMP-H and/or MLH1 silenced colon cancers. FIG. 13B shows the sensitivity and specificity of each of a seven gene panel plus CLDN1 in identifying BRAF mutant, CIMP-H and/or MLH1 silenced colon cancers.

SUMMARY

Figure 1A:
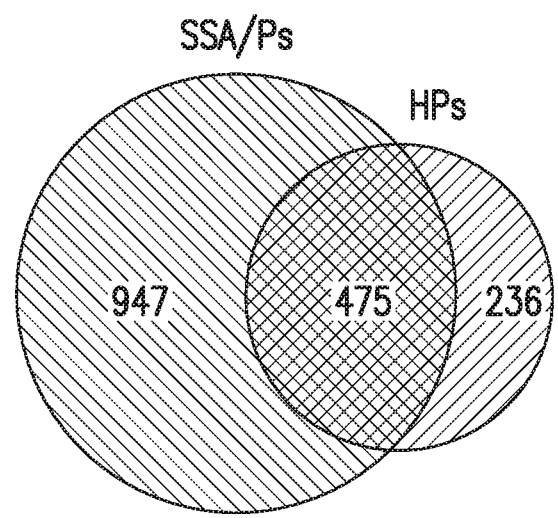
FIG. 1A-B shows differentially expressed annotated protein coding and non-coding RNAs in SSA/Ps and traditional hyperplastic polyps (HPs) identified by RNA sequencing.

Disclosed herein is a gene signature that differentiates SSA/Ps from HPs and shares a similar transcriptional profile with a subtype of colon cancers that can develop through the serrated pathway. Also, disclosed herein are composition and methods that can determine differentially expressed genes in SSA/Ps that is both sensitive and specific for detection of a BRAF mutant and CpG island methylator phenotype (CIMP-H) colon cancers.

Disclosed herein are methods of diagnosing a human subject with an increased susceptibility for colon cancer, the method comprising: a) obtaining a colon tissue sample in the subject; b) determining the mRNA expression level of FSCN1, ZIC2, ZIC5, CRYBA2, MUC6, TRNP1 and SEMG1 in the sample from the subject; c) obtaining a reference mRNA expression level for FSCN1, ZIC2, ZIC5, CRYBA2, MUC6, TRNP1 and SEMG1 for a normal control; d) comparing the expression level for FSCN1, ZIC2, ZIC5, CRYBA2, MUC6, TRNP1 and SEMG1 of step b) with the reference expression level for FSCN1, ZIC2, ZIC5, CRYBA2, MUC6, TRNP1 and SEMG1 of step c); and e) determining that the subject has an increased susceptibility to colon cancer wherein a ratio of the sample expression level of FSCN1, ZIC2, ZIC5, CRYBA2, MUC6, TRNP1 and SEMG1 to the reference expression level of FSCN1, ZIC2, ZIC5, CRYBA2, MUC6, TRNP1 and SEMG1 indicates higher expression level of FSCN1, ZIC2, ZIC5, CRYBA2, MUC6, TRNP1 and SEMG1 in the sample.

Disclosed herein are methods of diagnosing a human subject with an increased susceptibility for colon cancer, the method comprising: a) obtaining a colon tissue sample in the subject; b) determining the mRNA expression level of three or more of FSCN1, ZIC2, ZIC5, CRYBA2, MUC6, TRNP1 and SEMG1 in the sample from the subject; c) obtaining a reference mRNA expression level for the three or more FSCN1, ZIC2, ZIC5, CRYBA2, MUC6, TRNP1 and SEMG1 in b) for a normal control; d) comparing the expression level for three or more of FSCN1, ZIC2, ZIC5, CRYBA2, MUC6, TRNP1 and SEMG1 of step b) with the reference expression level for three or more of FSCN1, ZIC2, ZIC5, CRYBA2, MUC6, TRNP1 and SEMG1 of step c); and e) determining that the subject has an increased susceptibility to colon cancer wherein a ratio of the sample expression level of three or more of FSCN1, ZIC2, ZIC5, CRYBA2, MUC6, TRNP1 and SEMG1 to the reference expression level of three or more of FSCN1, ZIC2, ZIC5, CRYBA2, MUC6, TRNP1 and SEMG1 indicates higher expression level of three or more of FSCN1, ZIC2, ZIC5, CRYBA2, MUC6, TRNP1 and SEMG1 in the sample.

Disclosed herein are diagnostic devices, comprising biomarkers, wherein the biomarkers are FSCN1, ZIC2, ZIC5, CRYBA2, MUC6, TRNP1 and SEMG1.

Disclosed herein are gene expression panels for assessing risk of developing colon cancer in a human subject, consisting of primers or probes for detecting FSCN1, ZIC2, ZIC5, CRYBA2, MUC6, TRNP1 and SEMG1 in a sample.

DETAILED DESCRIPTION

The present disclosure can be understood more readily by reference to the following detailed description of the invention, the figures and the examples included herein.

Before the present methods and gene expression panels are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, and the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

Definitions

As used in the specification and the appended claims, the singular forms "a," "an" and "the" include plural referents unless the context clearly dictates otherwise.

The word "or" as used herein means any one member of a particular list and also includes any combination of members of that list.

Ranges can be expressed herein as from "about" or "approximately" one particular value, and/or to "about" or "approximately" another particular value. When such a range is expressed, a further aspect includes from the one particular value and/or to the other particular value. Similarly, when values are expressed as approximations, by use of the antecedent "about," or "approximately," it will be understood that the particular value forms a further aspect. It will be further understood that the endpoints of each of the ranges are significant both in relation to the other endpoint and independently of the other endpoint. It is also understood that there are a number of values disclosed herein and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed.

As used herein, the terms "optional" or "optionally" mean that the subsequently described event or circumstance may or may not occur and that the description includes instances where said event or circumstance occurs and instances where it does not.

As used herein, the term "sample" is meant a tissue or organ from a subject; a cell (either within a subject, taken directly from a subject, or a cell maintained in culture or from a cultured cell line); a cell lysate (or lysate fraction) or cell extract; or a solution containing one or more molecules derived from a cell or cellular material (e.g. a polypeptide or nucleic acid), which is assayed as described herein. A sample may also be any body fluid or excretion (for example, but not limited to, blood, urine, stool, saliva, tears, bile) that contains cells or cell components.

As used herein, the term "subject" refers to the target of administration, e.g., a human. Thus, the subject of the disclosed methods can be a vertebrate, such as a mammal, a fish, a bird, a reptile, or an amphibian. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). In one aspect, a subject is a mammal. In another aspect, a subject is a human. The term does not denote a particular age or sex. Thus, adult, child, adolescent and newborn subjects, as well as fetuses, whether male or female, are intended to be covered.

As used herein, the term "patient" refers to a subject afflicted with a disease or disorder. The term "patient" includes human and veterinary subjects. In some aspects of the disclosed methods, the "patient" has been diagnosed with a need for treatment for cancer, such as, for example, prior to the administering step.

As used herein, the term "comprising" can include the aspects "consisting of" and "consisting essentially of."

As used herein, the term "normal" refers to an individual, a sample or a subject that does not have colon cancer or does not have an increased susceptibility of developing colon cancer.

As used herein, the term "susceptibility" refers to the likelihood of a subject being clinically diagnosed with a disease. For example, a human subject with an increased susceptibility for colon cancer can refer to a human subject with an increased likelihood of a subject being clinically diagnosed with colon cancer.

As used herein, the term "polypeptide" refers to any peptide, oligopeptide, polypeptide, gene product, expression product, or protein. A polypeptide is comprised of consecutive amino acids. The term "polypeptide" encompasses naturally occurring or synthetic molecules. As used herein, the term "amino acid sequence" refers to a list of abbreviations, letters, characters or words representing amino acid residues.

As used herein, the term "gene" refers to a region of DNA encoding a functional RNA or protein. "Functional RNA" refers to an RNA molecule that is not translated into a protein. Generally, the gene symbol is indicated by using italicized styling while the protein symbol is indicated by using non-italicized styling.

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof By "isolated polypeptide" or "purified polypeptide" is meant a polypeptide (or a fragment thereof) that is substantially free from the materials with which the polypeptide is normally associated in nature. The polypeptides of the invention, or fragments thereof, can be obtained, for example, by extraction from a natural source (for example, a mammalian cell), by expression of a recombinant nucleic acid encoding the polypeptide (for example, in a cell or in a cell-free translation system), or by chemically synthesizing the polypeptide. In addition, polypeptide fragments may be obtained by any of these methods, or by cleaving full length polypeptides.

By "isolated nucleic acid" or "purified nucleic acid" is meant DNA that is free of the genes that, in the naturally-occurring genome of the organism from which the DNA of the invention is derived, flank the gene. The term therefore includes, for example, a recombinant DNA which is incorporated into a vector, such as an autonomously replicating plasmid or virus; or incorporated into the genomic DNA of a prokaryote or eukaryote (e.g., a transgene); or which exists as a separate molecule (for example, a cDNA or a genomic or cDNA fragment produced by PCR, restriction endonuclease digestion, or chemical or in vitro synthesis). It also includes a recombinant DNA which is part of a hybrid gene encoding additional polypeptide sequence. The term "isolated nucleic acid" also refers to RNA, e.g., an mRNA molecule that is encoded by an isolated DNA molecule, or that is chemically synthesized, or that is separated or substantially free from at least some cellular components, for example, other types of RNA molecules or polypeptide molecules.

By "specifically binds" is meant that an antibody recognizes and physically interacts with its cognate antigen (for example, a c-Met polypeptide) and does not significantly recognize and interact with other antigens; such an antibody may be a polyclonal antibody or a monoclonal antibody, which are generated by techniques that are well known in the art.

By "probe," "primer," or oligonucleotide is meant a single-stranded DNA or RNA molecule of defined sequence that can base-pair to a second DNA or RNA molecule that contains a complementary sequence (the "target"). The stability of the resulting hybrid depends upon the extent of the base-pairing that occurs. The extent of base-pairing is affected by parameters such as the degree of complementarity between the probe and target molecules and the degree of stringency of the hybridization conditions. The degree of hybridization stringency is affected by parameters such as temperature, salt concentration, and the concentration of organic molecules such as formamide, and is determined by methods known to one skilled in the art. Probes or primers specific for c-Met nucleic acids (for example, genes and/or mRNAs) have at least 80%-90% sequence complementarity, preferably at least 91%-95% sequence complementarity, more preferably at least 96%-99% sequence complementarity, and most preferably 100% sequence complementarity to the region of the c-Met nucleic acid to which they hybridize. Probes, primers, and oligonucleotides may be detectably-labeled, either radioactively, or non-radioactively, by methods well-known to those skilled in the art. Probes, primers, and oligonucleotides are used for methods involving nucleic acid hybridization, such as: nucleic acid sequencing, reverse transcription and/or nucleic acid amplification by the polymerase chain reaction, single stranded conformational polymorphism (SSCP) analysis, restriction fragment polymorphism (RFLP) analysis, Southern hybridization, Northern hybridization, in situ hybridization, electrophoretic mobility shift assay (EMSA).

By "specifically hybridizes" is meant that a probe, primer, or oligonucleotide recognizes and physically interacts (that is, base-pairs) with a substantially complementary nucleic acid (for example, a c-met nucleic acid) under high stringency conditions, and does not substantially base pair with other nucleic acids.

By "high stringency conditions" is meant conditions that allow hybridization comparable with that resulting from the use of a DNA probe of at least 40 nucleotides in length, in a buffer containing 0.5 M NaHPO$_4$, pH 7.2, 7% SDS, 1 mM EDTA, and 1% BSA (Fraction V), at a temperature of 65° C., or a buffer containing 48% formamide, 4.8×SSC, 0.2 M Tris-Cl, pH 7.6, 1×Denhardt's solution, 10% dextran sulfate, and 0.1% SDS, at a temperature of 42° C. Other conditions for high stringency hybridization, such as for PCR, Northern, Southern, or in situ hybridization, DNA sequencing, etc., are well-known by those skilled in the art of molecular biology. (See, for example, F. Ausubel et al., Current Protocols in Molecular Biology, John Wiley & Sons, New York, N.Y., 1998).

General

Serrated polyposis syndrome (SPS) is an extreme phenotype, with patients presenting with multiple SSA/Ps, and having a high risk of colon cancer (9-11). So far, no inherited gene mutation has been found in SPS. The risk of SSA/Ps progressing to colon cancer is not unique to SPS patients, and has also been described in patients with sporadic SSA/Ps (2, 12).

The "serrated polyp pathway" has been described as an underlying mechanism in the development of colon cancer from SSA/Ps and may account for 20-30% of sporadic colon cancers (6, 13-15). The molecular mechanisms or signaling pathways important in the progression of SSA/Ps to colon cancer, however, are uncertain. DNA microsatellite instability, CpG island methylation and BRAF mutations are possible underlying molecular mechanisms in the development of SSA/Ps (14-17). At least a subset of proximal colorectal cancers have the CpG island methylator phenotype (CIMP) and high microsatellite instability (MSI-H), suggesting similar molecular backgrounds in serrated polyps and proximal cancer (18).

Although limited information on gene expression profiles differentiating SSA/Ps from traditional hyperplastic polyps is available, two studies have described gene expression in SSA/Ps using microarray technologies (21, 22). More than 1200 differentially expressed genes in SSA/Ps from patients with SPS using RNA sequencing (RNA-seq) have been recently identified and several immunohistochemical markers specific for SSA/Ps have been developed (23). Comprehensive RNA-seq gene expression profiles, however, have not been defined for sporadic SSA/Ps, and it is not known whether they differ from syndromic SSA/Ps that have a high risk for progressing to colon cancer. Described herein is a panel of differentially expressed genes that discriminate between SSA/Ps and HPs and, a subset of SSA/P genes that are also differentially expressed in colon cancers that can develop through the serrated pathway. As further described herein, gene expression was compared in prospectively collected SSA/Ps from patients with SPS and sporadic SSA/Ps, HPs, tubular adenomas, and normal colon tissue to identify commonly expressed genes in SSA/Ps.

Sessile serrated adenoma/polyps (SSA/Ps) are recognized as polyps with malignant potential, with SSA/Ps originating in the serrated polyposis syndrome having the highest risk for progression to colon cancer. Recent cancer surveillance guidelines recommend earlier follow up for patients with sporadic SSA/Ps almost at par with individuals with adenomatous polyps (24). Nevertheless, differentiating SSA/Ps from HPs by histopathology and identifying patients with SSA/Ps have some challenges in clinical practice. As provided in the Examples section below, RNA sequencing datasets described herein was capable of identifying 51 differentially expressed genes in SSA/Ps that molecularly distinguishes them from HPs. Combinations of one or more of the genes identified below were also found to differentially expressed in sporadic microsatellite unstable (MSI-H) colon cancers. Also disclosed herein genes that show frequent overexpression in BRAF mutant, CpG island methylator phenotype high (CIMP-H) and MLH1 silenced colon cancers. The Examples described herein show that RNA expression changes in BRAF mutant, CIMP-H and MLH1 silenced colon cancers are observed in early SSA/Ps and that these new gene expression markers can lead to improved diagnostics for SSA/Ps. Moreover, the Examples described herein further demonstrate similar gene expression profiles of SSA/Ps in the serrated polyposis syndrome and sporadic SSA/Ps indicating that common mechanisms of progression to cancer are operating in both.

The Examples provide a comprehensive gene expression comparison of SSA/Ps with HPs, which share many histopathological similarities but differ markedly in risk of progression to colon cancer. Despite many similarities in gene expression in SSA/Ps and HPs, both sporadic and syndromic SSA/Ps have an individual gene signature with a number of highly differentially expressed genes of interest relative to oncogenesis. The identification of a set of novel genes commonly differentially expressed in SSA/Ps and BRAF mutant, CIMP-H and MLH1 silenced colon cancers provides additional information to further understand the molecular pathways leading to cancer progression via the serrated pathway. Together this may lead to the development of a gene panel that can be used in clinical practice to stratify patients with increased colon cancer risk from serrated polyps. A gene panel described herein can be helpful in identifying patients with serrated polyposis syndrome in whom no currently recognized genetic mutation has been identified.

Disclosed herein are compositions and methods that can be useful in diagnosing an increased susceptibility of colon cancer in a subject. Also described herein, are methods of predicting a colon cancer subtype comprising determining the mRNA expression level of three or more of FSCN1, ZIC2, ZIC5, CRYBA2, MUC6, TRNP1 and SEMG1 in the sample from a subject. Fascin actin-bundling protein 1 (FSCN1) is a gene encoding a fascin protein, a member of the fascin family of actin-binding proteins. This protein is involved in cell migration, motility, adhesion and cellular interactions. Upregulation or overexpression of FSCN1 is associated with lung metastasis likely resulting in increased cell motility. Zinc finger protein 2 (ZIC2; also known as HPES) is a gene encoding a protein in the ZIC family of C2H2-type zinc finger proteins. ZIC2 acts as a transcriptional repressor. ZIC2 mutations are linked to heart defects and holoprosencephaly. The ZIC family is important during development. ZIC2 is not found in normal (adult or fully developed) tissue. Zinc finger protein 5 (ZIC5) is a gene that also encodes a protein in the ZIC family of C2H2-type zinc finger proteins, and is closely linked to ZIC2. Similar to ZIC2, ZIC5 likely plays a role in development. ZIC5, like ZIC2, is not found in normal (adult or fully developed) tissue. Crystallin beta A2 (CRYBA2; also known as CTRCT42) protein. Mutations of CRYBA2 have been previously associated with cataracts. Mucin 6 (MUC6; also referred to as oligomeric mucus/gel-forming) encodes gastric mucin which functions in epithelial cytoprotection from acid, proteases, pathogenic microorganisms, and mechanical trauma in the gastrointestinal tract. TMF1-regulated nuclear protein 1 (TRNP1) is thought to function as a DNA-binding factor. For instance, TRNP1 may be linked to controlling proliferation rate of cells through the regulation of cell-cycle transition points. Semenogelin-1 (SEMG1) encodes a protein in semen.

Methods for Assessing Susceptibility and/or Diagnosis of Cancer

Disclosed herein, are methods for diagnosing a subject (e.g., human) with an increased susceptibility for colon cancer. The method comprises the steps of, in any order, a) obtaining a colon tissue sample in the subject; b) determining the mRNA expression level of one or more of FSCN1, ZIC2, ZIC5, CRYBA2, MUC6, TRNP1 and SEMG1 in the sample from the subject; c) obtaining a reference mRNA expression level for one or more of FSCN1, ZIC2, ZIC5, CRYBA2, MUC6, TRNP1 and SEMG1 for a normal control; d) comparing the expression level for FSCN1, ZIC2, ZIC5, CRYBA2, MUC6, TRNP1 and SEMG1 of step b) with the reference expression level for FSCN1, ZIC2, ZIC5, CRYBA2, MUC6, TRNP1 and SEMG1 of step c); and e) determining that the subject has an increased susceptibility to colon cancer wherein a ratio of the sample expression level of one or more of FSCN1, ZIC2, ZIC5, CRYBA2, MUC6, TRNP1 and SEMG1 to the reference expression level of one or more of FSCN1, ZIC2, ZIC5, CRYBA2, MUC6, TRNP1 and SEMG1 indicates higher expression level of one or more of FSCN1, ZIC2, ZIC5, CRYBA2, MUC6, TRNP1 and SEMG1 in the sample.

In an aspect, the method further comprises the step of providing a colonoscopy to the subject. The method described herein can also be carried out with one or more diagnostic tests (e.g., nucleic acid assay or protein assay). In an aspect, the method further comprises the detection of the presence or absence of a BRAF mutation. In an aspect, the method further comprises determining the expression level of MLH1. In some aspects, the method further comprises testing the subject with increased susceptibility to colon cancer to determine if the subject has an increased risk or susceptibility of developing or having colon cancer or has colon cancer. In an aspect, the method further comprises assaying the colon tissue sample to detect the presence of a BRAF mutation, wherein the ratio of the sample expression level of at least one of FSCN1, ZIC2, ZIC5, CRYBA2, MUC6, TRNP1 and SEMG1 to the reference expression of FSCN1, ZIC2, ZIC5, CRYBA2, MUC6, TRNP1 and SEMG1 is two-fold higher indicating an increased susceptibility of colon cancer in the subject. In an aspect, the method further comprises the step of determining the expression level of MLH1 in the sample from the subject. And, in another aspect, the method further comprises determining CpG island methylation of FSCN1, ZIC2, ZIC5, CRYBA2, MUC6, TRNP1 and SEMG1 in the sample from the subject.

Obtaining a Tissue Sample.

Procedures for the extraction and collection of a sample of a subject's colon tissue can be done by methods known in the art. Colon tissue obtained via biopsy is standard practice. Frozen tissue specimens can also be used. As noted above, tissue samples can be obtained from the subject's stool or using core needle biopsies. The sample can be whole cells or cell organelles. Cells can be collected by scraping the tissue, processing the tissue sample to release individual cells or isolating the cells from a bodily fluid. The sample can be fresh tissue, dry tissue, cultured cells or tissue. The sample can be unfixed or fixed. Any part of the colon can be obtained and assessed using the methods described herein. In an aspect, the colon tissue is from a sessile serrated adenoma/polyp.

Determining mRNA Expression Level.

As used herein, the term "expression," when used in the context of determining or detecting the expression or expression level of one or more genes, can refer to determining or detecting transcription of the gene (i.e., determining mRNA levels) and/or determining or detecting translation of the gene (e.g., determining or detecting the protein produced). To determine the expression level of a gene means to determine whether or not a gene is expressed, and if expressed, to what relative degree.

The expression level of one or more genes disclosed herein can be determined directly (e.g., immunoassays, mass spectrometry) or indirectly (e.g., determining the mRNA expression of a protein or peptide). Examples of mass spectrometry include ionization sources such as EI, CI, MALDI, ESI, and analysis such as Quad, ion trap, TOF, FT or combinations thereof, spectrometry, isotope ratio mass spectrometry (IRMS), thermal ionization mass spectrometry (TIMS), spark source mass spectrometry, Multiple Reaction Monitoring (MRM) or SRM. Any of these techniques can be carried out in combination with prefractionation or enrichment methods. Examples of immunoassays include immunoblots, Western blots, Enzyme linked Immunosorbant Assay (ELISA), Enzyme immunoassay (EIA), radioimmune assay.

Immunoassay methods use antibodies for detection and determination of levels of an antigen are known in the art. The antibody can be immobilized on a solid support such as a stick, plate, bead, microbead or array.

Expression levels of one or more of the genes described herein can be also be determined indirectly by determining the mRNA expression for the one or more genes in a tissue sample. RNA expression methods include but are not limited to extraction of cellular mRNA and Northern blotting using labeled probes that hybridize to transcripts encoding all or part of the gene, amplification of mRNA using gene-specific primers, polymerase chain reaction (PCR), and reverse transcriptase-polymerase chain reaction (RT-PCR), followed by quantitative detection of the gene product by a variety of methods; extraction of RNA from cells, followed by labeling, and then used to probe cDNA or olignonucleotides encoding the gene, in situ hybridization; and detection of a reporter gene.

Methods to measure protein expression levels include but are not limited to Western blot, immunoblot, ELISA, radio-immunoassay, immunoprecipitation, surface plasmon resonance, chemiluminescence, fluorescent polarization, phosphorescence, immunohistochemical analysis, microcytometry, microarray, microscopy, fluorescence activated cell sorting (FACS), and flow cytometry. The method can also include specific protein property-based assays based including but not limited to enzymatic activity or interaction with other protein partners. Binding assays can also be used, and are well known in the art. For instance, a BIAcore machine can be used to determine the binding constant of a complex between two proteins. Other suitable assays for determining or detecting the binding of one protein to another include, immunoassays, such as ELISA and radioimmunoassays. Determining binding by monitoring the change in the spectroscopic can be used or optical properties of the proteins can be determined via fluorescence, UV absorption, circular dichroism, or nuclear magnetic resonance (NMR). Alternatively, immunoassays using specific antibody can be used to detect the expression on of a particular protein on a tumor cell.

Reference mRNA Expression Level.

As used herein, the term "reference," "reference expression," "reference sample," "reference value," "control," "control sample" and the like, when used in the context of a sample or expression level of one or more genes or proteins refers to a reference standard wherein the reference is expressed at a constant level among different (i.e., not the same tissue, but multiple tissues) tissues, and is unaffected by the experimental conditions, and is indicative of the level in a sample of a predetermined disease status (e.g., not suffering from colon cancer). The reference value can be a predetermined standard value or a range of predetermined standard values, representing no illness, or a predetermined type or severity of illness.

Reference expression can be the level of the one or more genes described herein in a reference sample from a subject, or a pool of subjects, not suffering from colon cancer or from a predetermined severity or type of colon cancer. In an aspect, the reference value is the level of one or more genes disclosed herein in the tissue of a subject, or subjects, wherein the subject or subjects is not suffering from colon cancer.

Comparing the Expression Level of One or More Genes Disclosed Herein.

By comparing the expression level for one or more of, for example, FSCN1, ZIC2, ZIC5, CRYBA2, MUC6, TRNP1 and SEMG1 of step b) with the reference expression level for, for example, FSCN1, ZIC2, ZIC5, CRYBA2, MUC6, TRNP1 and SEMG1 of step c), it is possible to determine a subject's susceptibility to colon cancer.

Determining the expression level of one or more genes disclosed herein can include determining whether the gene is upregulated or increased as compared to a control or reference sample, downregulated or decreased compared to a control or reference sample, or unchanged compared to a control or reference sample. As used herein, the terms, "upregulated" and "increased expression level" or "increased level of expression" refers to a sequence corresponding to one or more genes disclosed herein that is expressed wherein the measure of the quantity of the sequence exhibits an increased level of expression when compared to a reference sample or "normal" control. For example, the terms, "upregulated" and "increased expression level" or "increased level of expression" refers to a sequence corresponding to one or more genes disclosed herein that is expressed wherein the measure of the quantity of the sequence exhibits an increased level of expression of one or more of FSCN1, ZIC2, ZIC5, CRYBA2, MUC6, TRNP1 and SEMG1 protein(s) and/or mRNA when compared to the expression of the same mRNA(s) from a reference sample or "normal" control. An "increased expression level" refers to an increase in expression of at least 1%, 2%, 3%, 4%, 5%, 6%, 7%, 8%, 9%, 10% or more, for example, 20%, 30%, 40%, or 50%, 60%, 70%, 80%, 90% or more, or greater than 1-fold, up to 2-fold, 3-fold, 4-fold, 5-fold, 10-fold, 50-fold, 100-fold or more. As used herein, the terms "downregulated," "decreased level of expression," or "decreased expression level" refers to a sequence corresponding to one or more genes disclosed herein that is expressed wherein the measure of the quantity of the sequence exhibits a decreased level of expression when compared to a reference sample or "normal" control For example, the terms "downregulated," "decreased level of expression," or "decreased expression level" refers to a sequence corresponding to one or more genes disclosed herein that is expressed wherein the measure of the quantity of the sequence exhibits a decreased level of expression of one or more of FSCN1, ZIC2, ZIC5, CRYBA2, MUC6, TRNP1, SEMG1 and MCL1 protein(s) and/or mRNA when compared to the expression of the same mRNA(s) from a reference sample or "normal" control. A "decreased level of expression" refers to a decrease in expression of at least 1%, 2%, 3%, 4%, 5%, 6%, 7%, 8%, 9%, 10% or more, for example, 20%, 30%, 40%, or 50%, 60%, 70%, 80%, 90% or more, or greater than 1-fold, up to 2-fold, 3-fold, 4-fold, 5-fold, 10-fold, 50-fold, 100-fold or more.

Determining an Increased Susceptibility to Colon Cancer.

As described herein, samples from a subject can be compared with reference samples to determine the expression ratio to determine whether a subject has an increased susceptibility to colon cancer. The reference samples can be from subjects having "normal" levels of one or more of the following genes, FSCN1, ZIC2, ZIC5, CRYBA2, MUC6, TRNP1 and SEMG1. Suitable statistical and other analysis can be carried out to confirm a change (e.g., an increase or a higher level of expression) in one or more of FSCN1, ZIC2, ZIC5, CRYBA2, MUC6, TRNP1 and SEMG1 when compared with a reference sample, wherein a ratio of the sample expression level of one or more of FSCN1, ZIC2, ZIC5, CRYBA2, MUC6, TRNP1 and SEMG1 to the reference expression level of one or more of FSCN1, ZIC2, ZIC5, CRYBA2, MUC6, TRNP1 and SEMG1 indicates higher expression level of one or more of FSCN1, ZIC2, ZIC5, CRYBA2, MUC6, TRNP1 and SEMG1 in the sample.

In an aspect, the ratio of the sample expression level of two or more, three or more, four or more, five or more, or six or more of FSCN1, ZIC2, ZIC5, CRYBA2, MUC6, TRNP1 and SEMG1 to the reference expression level of two or more, three or more, four or more, five or more, or six or more of FSCN1, ZIC2, ZIC5, CRYBA2, MUC6, TRNP1 and SEMG1 indicates higher expression level of two or more, three or more, four or more, five or more, or six or more of FSCN1, ZIC2, ZIC5, CRYBA2, MUC6, TRNP1 and SEMG1 in the sample, indicating that the subject has an increased susceptibility to colon cancer.

A higher or increased expression level of one or more of FSCN1, ZIC2, ZIC5, CRYBA2, MUC6, TRNP1 and SEMG1 when compared to the reference expression level of FSCN1, ZIC2, ZIC5, CRYBA2, MUC6, TRNP1 and SEMG1 can indicate an increased susceptibility to colon cancer. Signature pattern(s) of increased (higher) or decreased (lower) sample expression levels of one or more of FSCN1, ZIC2, ZIC5, CRYBA2, MUC6, TRNP1 and SEMG1 when compared to the reference expression levels of one or more of FSCN1, ZIC2, ZIC5, CRYBA2, MUC6, TRNP1 and SEMG1 can be observed and indicate the susceptibility (e.g., higher or lower) of colon cancer in a subject.

The expression level of one or more genes described herein can be a measure of one or more genes, for example, per unit weight or volume. In an aspect, the expression level can be a ratio (e.g., the amount of one or more genes in a sample relative to the amount of the one or more markers of a reference value).

In some aspects, samples from a subject can be compared with reference samples to determine the percent change to determine whether a subject has an increased susceptibility to colon cancer. In other words, the expression level can be expressed as a percent. For example, the percent change in the expression levels of one or more genes, wherein the expression level of one (or two, three, four, five or six) or more of FSCN1, ZIC2, ZIC5, CRYBA2, MUC6, TRNP1 and SEMG1 is increased (or is higher) by 10%, 15%, 20%, 25%, 30%, 35%, 40%, 45%, 50%, 55%, 60%, 65%, 70%, 75%, 80%, 85%, 90%, 95%, or 100% when compared to the reference expression level of FSCN1, ZIC2, ZIC5, CRYBA2, MUC6, TRNP1 and SEMG1, indicating an increased susceptibility to colon cancer. Alternatively, the percent change in the expression levels of one or more genes can be decreased (or lower) by 10%, 15%, 20%, 25%, 30%, 35%, 40%, 45%, 50%, 55%, 60%, 65%, 70%, 75%, 80%, 85%, 90%, 95%, or 100% when compared to a reference expression level.

In some aspects, an increase or decrease or some combination thereof in the expression level of genes or proteins other than those disclosed herein can indicate an increased susceptibility for colon cancer or a diagnosis of colon cancer in a subject. In some aspects, a signature pattern of increased or decreased expression levels of one or more of the genes or proteins disclosed herein is indicative.

In aspect, the methods disclosed herein can further include a method of prevention of colon cancer morbidity and/or mortality. For example, the method comprises providing to a subject, further testing (which can include testing for cancer), such as, for example, a colonoscopy, and/or a routine physical examination, wherein an increased susceptibility to colon cancer has been diagnosed. The method can further include the administration of therapy to prevent colon cancer from developing or spreading, thereby reducing colon cancer morbidity and/or mortality.

The methods described herein can further comprise the step of assaying the colon tissue sample from the subject to detect the presence of other molecular features of colon cancer. In some aspects, the method can further comprise the step of assaying the colon tissue sample from the subject to detect the presence of a BRAF mutation. In an aspect, wherein a BRAF mutation is detected in the sample, the ratio (or percent change) of the sample expression level of at least one of FSCN1, ZIC2, ZIC5, CRYBA2, MUC6, TRNP1 and SEMG1 to reference expression of the same gene is two-fold higher (or more) indicating an increased susceptibility of colon cancer in the subject.

BRAF is a part of the Ras/Raf/MEK/MAP signal transduction pathway, and oncogenic mutations in BRAF, including but not limited to the V600E mutation, have been reported in various types of cancer, including colon cancer. A BRAF mutation has also been observed in the majority of all microsatellite-unstable carcinomas; and in a subset of microsatellite stable colon tumors. A variety of methods can be used to detect BRAF in a sample including single-strand conformation analysis, DNA sequencing, TaqMan-based real-time PCR, real-time allele-specific PCR, pyrosequencing, and oligonucleotide microarray. In an aspect, BRAF mutation detection can be carried out using quantitative RT-PCR.

It is well-known that the majority of stable and unstable cancers with a BRAF mutation also have diffuse methylation of CpG islands also referred to as CpG island methylator phenotype (CIMP). CpG islands are regions of DNA with a high frequency of cytosine nucleotides next to a guanine nucleotide, separated by one phosphate, in a linear sequence. In an aspect, the method described herein can further comprise the step of determining CpG island methylation or the existence of CIMP with of one or more of FSCN1, ZIC2, ZIC5, CRYBA2, MUC6, TRNP1 and SEMG1 in the sample from the subject.

In some aspects, the methods described herein can further include the step of determining the relationship between CIMP status and other molecular features of colon cancer including but not limited to BRAF mutation and MSI status. CIMP status can be determined in any number of ways known to one of ordinary skill in the art, as a standard method has yet to be established.

Colon cancers can be classified based on the presence of a microsatellite or a series of repetitive DNA (e.g., DNA motifs) ranging from two to five nucleotides repeated 5 to 50 times. Microsatellites are recognized to have a high mutation rate, and can be used for DNA profiling.

MSI results from an impaired DNA mismatch repair (MMR), and the presence of the MSI phenotype indicates that DNA mismatch repair is not operating normally. Microsatellite instability (MSI) phenotype can be further classified as high (MSI-H) or low (MSI-L). For example, MSI-H means that a tumor is MMR deficient, while MSI-L means that a tumor is MMR proficient. Microsatellite stability (MSS) refers to cancers or profiles that any defect in the mismatch repair system is unlikely.

MLH1 protein is a DNA mismatch repair protein. Deficient expression or silencing of MLH1 in colon cancer has been reported. In an aspect, the method disclosed herein can further comprise determining the expression level of MLH1 in the sample from the subject. The methods disclosed herein can further include the step of determining the expression level or presence of MLH1 in sample along with determining CIMP status, the presence of a BRAF mutation or MSI status or a combination thereof. A downregulation or a decreased expression level of MLH1 in a sample can indicate an increased susceptibility to colon cancer. In an aspect, a downregulation or a decreased expression level of MLH1 in a sample can indicate colon cancer.

Diagnostic Device

Disclosed herein, is a diagnostic device for diagnosing or assessing the risk of developing colon cancer in a subject (e.g., human). In an aspect, a sample of tissue can be obtained from the subject and the level or expression level in the sample can be compared with a reference value.

The diagnostic device can include one or more biomarkers. Biomarkers can bind to or hybridize with one or more genes disclosed herein, RNA products or peptides. As used herein, the terms "marker" or "biomarker" refers to detectable or measurable substance (e.g., gene, gene product, protein, etc.) in a sample that can indicate a biological state, disease, condition, predict a clinical outcome, etc. In an aspect, biomarkers can be FSCN1, ZIC2, ZIC5, CRYBA2, MUC6, TRNP1, SEMG1 and MLH1 or FSCN1, ZIC2, ZIC5, CRYBA2, MUC6, TRNP1, SEMG1 and MLH1 or a fragment thereof, or an antibody or fragment thereof which binds one or more of the biomarkers. The diagnostic device can be incorporated into a kit for diagnosing or assessing the risk of developing colon cancer in a subject.

Protein Array

Disclosed herein are polypeptide or protein arrays. In an aspect, the protein arrays can comprise probes including antibodies, aptamers, and other cognate binding ligands specific to a component of the gene panels disclosed herein. Protein arrays and methods of constructing the protein arrays are well known to one of ordinary skill in the art.

One type of protein array that can be suitable uses an immobilized "capture antibody." The polypeptides are bound to a solid substrate (e.g., glass) with a treated surface (e.g., aminosilane) or through a biotin-streptavidin conjugation. The arrays are then incubated with a solution containing probe that can bind to the capture antibodies in a manner dependent upon time, buffer components, and recognition specificity. The probes can then be visualized directly if they have been previously labeled, or can be bound to a secondary labeled reagent (e.g., another antibody). The amount of probe bound to the capture antibody that is visualized can depend upon the labeling method utilized; generally, a CCD imager or laser scanner that uses filter sets that are appropriate to excite and detect the emissions of the label can be used. The imager converts the amount of detected photons into an electronic signal (often an 8-bit or 16-bit scale) that can be analyzed using commercially available software packages.

The substrate of the array can be organic or inorganic, biological or non-biological or any combination of these materials. The substrate can be transparent or translucent. Examples of materials suitable for use as a substrate in the array include silicon, silica, quartz, glass, controlled pore glass, carbon, alumina, titanium dioxide, germanium, silicon nitride, zeolites, and gallium arsenide; and metals including gold, platinum, aluminum, copper, titanium, and their alloys. Ceramics and polymers can also be used as substrates. Suitable polymers include, but are not limited to polystyrene; poly(tetra)fluorethylene; (poly)vinylidenedifluoride; polycarbonate; polymethylmethacrylate; polyvinylethylene; polyethyleneimine; poly(etherether)ketone; polyoxymethylene (POM); polyvinylphenol; polylactides; polymethacrylimide (PM I); polyalkenesulfone (PAS); polyhydroxyethylmethacrylate; polydimethylsiloxane; polyacrylamide; polyimide; co-block-polymers; and Eupergit®. Photoresists, polymerized Langmuir-Blodgett films, and LIGA structures can also serve as substrates.

The array can further comprise a coating that can be formed on the substrate or applied to the substrate. The substrate can be modified with a coating by using thin-film technology based on either physical vapor deposition (PVD) or plasma-enhanced chemical vapor deposition (PECVD). Alternatively, plasma exposure can be used to directly activate the substrate. For instance, plasma etch procedures can be used to oxidize a polymeric surface (i.e. polystyrene or polyethylene to expose polar functionalities such as hydroxyls, carboxylic acids, aldehydes and the like).

The coating can comprise a metal film. Examples of metal films include aluminum, chromium, titanium, nickel stainless steel zinc, lead, iron, magnesium, manganese, cadmium, tungsten, cobalt, and alloys or oxides thereof. In an aspect, the metal film can be a noble metal film. Examples of noble metals that can be used for a coating include, but are not limited to, gold, platinum, silver, copper, and palladium. In an aspect, the coating comprises gold or a gold alloy. Electron-beam evaporation can be used to provide a thin coating of gold on the surface. In an aspect, the metal film can from about 50 nm to about 500 nm in thickness.

Alternatively, the coating can be silicon, silicon oxide, silicon nitride, silicon hydride, indium tin oxide, magnesium oxide, alumina, glass, hydroxylated surfaces, and a polymer.

The arrays described herein can comprise a collection of addressable elements. Such elements can be spacially addressable, such as arrays contained within microtiter plates or printed on planar surfaces wherein each element can be present at distinct X and Y coordinates. Alternatively, elements can be addressable based on tags, beads, nanoparticles, or physical properties. The microarrays can be prepared according to the methods known to one of ordinary skill in the art. The term "arrays" as used herein can refer to any biologic assay with multiple addressable elements. In an aspect, the addressable elements can be polypeptides (e.g., antibodies or fragments thereof) or nucleic acid probes. As used herein, "elements" refer to any probe (polypeptide or nucleic acid based) that can be bound by an organ-specific polypeptide, polypeptide fragment or transcript encoding such polypeptides, as related or associated with any of the gene or proteins disclosed herein. Molecules can be, but are not limited to, proteins, polypeptides, peptides, RNA, DNA, lipids, glycosylated molecules, carbohydrates, polypeptides with phosphorylation modifications, and polypeptides with citrulline modifications, aptamers, oxidated molecules, and other molecules.

For the elements described herein, "addressability" refers to the location, position, tags, cleavable tags or markers, identifiers, spectral properties, electrophoretic properties, or other physical properties that enable identification of the element. An example of addressability, also known as coding, is spatial addressability, where the position of the molecule is fixed, and that position is correlated with the identity. This type of spatial array can generally be synthesized or spotted onto a planar substrate, producing, for example, microarrays, where a large number of different molecules are densely laid out in a small area (e.g. comprising at least about 400 different sequences per cm2, and can be 1000 sequences per $cm^2$ or as many as 5000 sequences per $cm^2$, or more). Less dense arrays (e.g., ELISA or RIA plates) where wells in a plate each contain a distinct probe can comprise from about 96 sequences per plate, up to about 100 sequences per $cm^2$, up to the density of a microarray. Other spatial arrays utilize fiber optics, where distinct probes can be bound to fibers, which can be formed into a bundle for binding and analysis. Methods for the manufacture and use of spatial arrays of polypeptides are known in the art.

An alternative to this type of spatial coding array is the use of molecular "tags," where the target probes can be attached to a detectable label, or tag, which can provide coded information about the sequence of the probe. These tags can be cleaved from the element, and subsequently detected to identify the element. In an aspect, a set of probes can be synthesized or attached to a set of coded beads, wherein each bead can be linked to a distinct probe, and wherein the beads can be coded in a manner that allows identification of the attached probe. In this type of "tag array," flow cytometry can be used for detection of binding. For example, microspheres having fluorescence coding and can identify a particular microsphere. The probe can be covalently bound to a "color coded" object. A labeled target polypeptide can be detected by flow cytometry, and the coding on the microsphere can be used to identify the bound probe (e.g., immunoglobulin, antigen binding fragments of immunoglobulins, or ligands).

In an aspect, the array can be an immunoglobulin (e.g., antibody or antigen-binding fragment thereof) array. As used herein, an "immunoglobulin array" refers to a spatially separated set of discrete molecular entities capable of binding to target polypeptides arranged in a manner that allows identification of the polypeptides contained within the sample. In an aspect, the array can comprise one or more of proteins, polypeptides, peptides, RNA, DNA, lipid, glycosylated molecules, polypeptides with phosphorylation modifications, and polypeptides with citrulline modifications, aptamers, and other molecules.

Kits

In an aspect, kits are provided for measuring the RNA (e.g., a RNA product) of one or more biomarkers disclosed herein. The kits can comprise materials and reagents that can be used for measuring the expression of the RNA of one or more biomarkers. Examples of suitable kits include RT-PCR or microarray. These kits can include the reagents needed to carry out the measurements of the RNA expression levels. Alternatively, the kits can further comprise additional materials and reagents. For example, the kits can comprise materials and reagents required to measure RNA expression levels of any number of genes up to 1, 2, 3, 4, 5, 10, or more genes that are not biomarkers disclosed herein.

Gene Expression Panel

Disclosed herein are gene expression panels and arrays for assessing risk of developing colon cancer in a subject (e.g., human) consisting of primers or probes capable of detecting one or more genes disclosed herein. The disclosed gene expression panels or arrays can comprise any of the genes disclosed herein. For example, the gene expression panel or array can be used to detect one or more of FSCN1, ZIC2, ZIC5, CRYBA2, MUC6, TRNP1, SEMG1 and MLH1. In an aspect, the gene expression panels or arrays can comprise FSCN1, ZIC2, ZIC5, CRYBA2, MUC6, TRNP1, and SEMG1.

In an aspect, the sample is colon tissue. The colon tissue can be from a sessile serrated adenoma/polyp.

The gene expression panels or arrays disclosed herein can consist of primers or probes capable of detecting or amplifying any number of the genes disclosed herein. The gene expression panels or arrays disclosed herein can further comprise primers or probes capable of detecting or amplifying any number of genes not disclosed herein. For example, the primers or probes can detect or amplify between 1 and 5, 5 and 10, 10 and 100, or more, or any variation in between.

The gene expression panels or arrays disclosed herein can be used as a standalone method for assessing risk of developing colon cancer in a subject or in combination with one or more other gene expression panels or arrays not disclosed herein. They can be used along with one or more diagnostic test. In an aspect, the gene expression panels or arrays can further comprise a second diagnostic test. The gene expression panels or arrays disclosed herein can also be used in methods to generate a specific profile. The profile can be provided in the form of a heatmap or boxplot.

The profile of the gene expression levels can be used to compute a statistically significant value based on differential expression of the one or more genes disclosed herein, wherein the computed value correlates to a diagnosis for a subtype of colon cancer. The variance in the obtained profile of expression levels of the said selected genes or gene expression products can be either upregulated or downregulated in subjects with an increased susceptibility compared to a reference subject or control. The Examples section provides additional detail. For instance, when the expression level of one or more of FSCN1, ZIC2, ZIC5, CRYBA2, MUC6, TRNP1, and SEMG1 are upregulated, indicating an increased risk of developing colon cancer. When the expression level of MLH1, for instance, is downregulated, this can also indicate an increased risk of developing colon cancer. As described herein, one of ordinary skill in the art can use a combination of any of genes disclosed herein to form a profile that can then be used to assess risk of developing colon cancer, or to determine (and diagnose) whether a subject has colon cancer.

Disclosed herein are methods of diagnosing colon cancer using the gene expression panel or array described herein. In an aspect, the method further comprises performing a colonoscopy.

In an aspect, the gene expression panel or array disclosed herein can be used to determine or assess the risk of developing colon cancer in a subject, wherein the expression level for FSCN1, ZIC2, ZIC5, CRYBA2, MUC6, TRNP1, and SEMG1 in the sample is compared to a reference expression level for FSCN1, ZIC2, ZIC5, CRYBA2, MUC6, TRNP1, and SEMG1. In an aspect, the gene expression panel or array disclosed herein can be used to determine or assess the risk of developing colon cancer in a subject, wherein a ratio (or percent change) of the sample expression level of one or more of FSCN1, ZIC2, ZIC5, CRYBA2, MUC6, TRNP1 and SEMG1 to the reference expression level of one or more of FSCN1, ZIC2, ZIC5, CRYBA2, MUC6, TRNP1 and SEMG1 indicates higher expression level of one or more of FSCN1, ZIC2, ZIC5, CRYBA2, MUC6, TRNP1 and SEMG1 in the sample. In an aspect, the ratio (or percent change) of the sample expression level of two or more, three or more, four or more, five or more, or six or more of FSCN1, ZIC2, ZIC5, CRYBA2, MUC6, TRNP1 and SEMG1 to the reference expression level of two or more, three or more, four or more, five or more, or six or more of FSCN1, ZIC2, ZIC5, CRYBA2, MUC6, TRNP1 and SEMG1 indicates higher expression level of two or more, three or more, four or more, five or more, or six or more of FSCN1, ZIC2, ZIC5, CRYBA2, MUC6, TRNP1 and SEMG1 in the sample, indicating that the subject has an increased susceptibility to colon cancer. Suitable statistical and other analysis can be carried out to confirm a change (e.g., an increase or a higher level of expression) in one or more of FSCN1, ZIC2, ZIC5, CRYBA2, MUC6, TRNP1 and SEMG1 when compared with a reference sample.

The gene expression panel or array can consist of primers or probes capable of detecting, amplifying or otherwise measuring the presence or expression of one or more genes disclosed herein. For example, specific primers that can be used in the methods disclosed herein include, but are not limited to the primers suitable for use in the standard exon array from the Affymetrix website listed at: http://www.affymetrix.com. In an aspect, the gene expression panel or array disclosed herein for can be used to determine or assess the risk of developing colon cancer in a subject, wherein FSCN1, ZIC2, ZIC5, CRYBA2, MUC6, TRNP1 and SEMG1 RNA expression levels are detected in the sample.

In an aspect, a diagnostics kit is disclosed comprising one or more probes or primers capable of detecting, amplifying or measuring the presence or expression of one or more genes disclosed herein.

Disclosed herein, are solid supports comprising one or more primers, probes, polypeptides, or antibodies capable of hybridizing or binding to one or more of the genes disclosed herein. Solid supports are solid state substrates or supports that molecules, such as analytes and analyte binding molecules, can be associated. Analytes (e.g, calcifying nanoparticles and proteins) can be associated with solid supports directly or indirectly. For example, analytes can be directly immobilized on solid supports. Analyte capture agents (e.g., capture compounds) can also be immobilized on solid supports.

As mentioned above, one of ordinary skill in the art can determine the expression level of one or more genes (or proteins) disclosed herein any number of ways. To detect or quantify the level of RNA products of the biomarkers within a sample, arrays, such as microarrays, RT-PCR (including quantitative RT-PCR), nuclease protection assays and Northern blot analyses can be used. Accordingly, in an aspect, the biomarker expression levels can be determined using arrays, microarrays, RT-PCR, quantitative RT-PCR, nuclease protection assays or Northern blot analyses.

An array is a form of solid support. An array detector is also a form of solid support to which multiple different capture compounds or detection compounds have been coupled in an array, grid, or other organized pattern.

Solid-state substrates for use in solid supports can include, for instance, any solid material to which molecules can be coupled. Examples of such materials include acrylamide, agarose, cellulose, nitrocellulose, glass, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, poly lactic acid, polyorthoesters, polypropylfumerate, collagen, glycosaminoglycans, and polyamino acids. Solid-state substrates can have any useful form including thin film, membrane, bottles, dishes, fibers, woven fibers, shaped polymers, particles, beads, microparticles, or any combination thereof. Solid-state substrates and solid supports can be porous or non-porous. An example of a solid-state substrate is a microtiter dish (e.g., a standard 96-well type). A multiwell glass slide can also be used. For example, such as one containing one array per well can be used, allowing for greater control of assay reproducibility, increased throughput and sample handling, and ease of automation.

Different compounds can be used together as a set. The set can be used as a mixture of all or subsets of the compounds used separately in separate reactions, or immobilized in an array. Compounds used separately or as mixtures can be physically separable through, for example, association with or immobilization on a solid support. An array can include a plurality of compounds immobilized at identified or predefined locations on the array. Each predefined location on the array can generally have one type of component (that is, all the components at that location are the same). Each location can have multiple copies of the component. The spatial separation of different components in the array allows separate detection and identification of the polynucleotides or polypeptides disclosed herein.

It is not required that a given array be a single unit or structure. The set of compounds can be distributed over any number of solid supports. For example, each compound can be immobilized in a separate reaction tube or container, or on separate beads or microparticles. Different aspects of the disclosed method and use of the gene expression panel or array or diagnostic device can be performed with different components (e.g., different compounds specific for different proteins) immobilized on a solid support.

Some solid supports can have capture compounds, such as antibodies, attached to a solid-state substrate. Such capture compounds can be specific for calcifying nanoparticles or a protein on calcifying nanoparticles. Captured calcified nanoparticles or proteins can then be detected by binding of a second detection compound, such as an antibody. The detection compound can be specific for the same or a different protein on the calcifying nanoparticle.

Methods for immobilizing nucleic acids, peptides or antibodies (and other proteins) to solid-state substrates are well established. Immobilization can be accomplished by attachment, for example, to aminated surfaces, carboxylated surfaces or hydroxylated surfaces using standard immobilization chemistries. Examples of attachment agents are cyanogen bromide, succinimide, aldehydes, tosyl chloride, avidinbiotin, photocrosslinkable agents, epoxides, maleimides and N-[y-Maleimidobutyryloxy] succinimide ester (GMBS), and a heterobifunctional crosslinker. Antibodies can be attached to a substrate by chemically cross-linking a free amino group on the antibody to reactive side groups present within the solid-state substrate. Antibodies can be, for example, chemically cross-linked to a substrate that contains free amino, carboxyl, or sulfur groups using glutaraldehyde, carbodiimides, or GMBS, respectively, as cross-linker agents. In this method, aqueous solutions containing free antibodies can be incubated with the solid-state substrate in the presence of glutaraldehyde or carbodiimide.

A method for attaching antibodies or other proteins to a solid-state substrate is to functionalize the substrate with an amino- or thiol-silane, and then to activate the functionalized substrate with a homobifunctional cross-linker agent such as (Bis-sulfo-succinimidyl suberate (BS3) or a heterobifunctional cross-linker agent such as GMBS. For cross-linking with GMBS, glass substrates can be chemically functionalized by immersing in a solution of mercaptopropyltrimethoxysilane (1% vol/vol in 95% ethanol pH 5.5) for 1 hour, rinsing in 95% ethanol and heating at 120° C. for 4 hrs. Thiol-derivatized slides can be activated by immersing in a 0.5 mg/ml solution of GMBS in 1% dimethylformamide, 99% ethanol for 1 hour at room temperature. Antibodies or proteins can be added directly to the activated substrate, which can be blocked with solutions containing agents such as 2% bovine serum albumin, and air-dried. Other standard immobilization chemistries are known by those of ordinary skill in the art.

Each of the components (e.g., compounds) immobilized on the solid support can be located in a different predefined region of the solid support. Each of the different predefined regions can be physically separated from each other. The distance between the different predefined regions of the solid support can be either fixed or variable. For example, in an array, each of the components can be arranged at fixed distances from each other, while components associated with beads will not be in a fixed spatial relationship. The use of multiple solid support units (e.g., multiple beads) can result in variable distances.

Components can be associated or immobilized on a solid support at any density. Components can be immobilized to the solid support at a density exceeding 400 different components per cubic centimeter. Arrays of components can have any number of components. For example, an array can have at least 1,000 different components immobilized on the solid support, at least 10,000 different components immobilized on the solid support, at least 100,000 different components immobilized on the solid support, or at least 1,000,000 different components immobilized on the solid support.

In addition, the genes described herein can also be used as markers (i.e., biomarkers) for susceptibility to or presence or progression of colon cancer. The methods and assays described herein can be performed over time, and the change in the level of the markers assessed. For example, the assays can be performed every 24-72 hours for a period of 6 months to 1 year, and thereafter carried out as needed. Assays can also be completed prior to, during, or after a treatment protocol. Together, the genes disclosed herein can be used to profile an individual's risk or progression of colon cancer. As used within this context, the terms "differentially expressed" or "differential expression" refers to difference in the level of expression of the biomarkers disclosed herein that can be assayed by measuring the level of expression of the products (e.g., RNA or gene product) of the biomarkers, such as the difference in level of messenger RNA transcript or a portion thereof expressed or of proteins expressed of the biomarkers. In an aspect, this difference is significantly different.

To improve sensitivity, more than one gene disclosed herein can be assayed within a given sample. Binding agents specific for different proteins, antibodies, nucleic acids provided herein can be combined within a single assay. Further, multiple primers or probes can be used concurrently. To assist with such assays, specific biomarkers can assist in the specificity of such tests.

Levels of expression can be measured at the transcriptional and/or translational levels. At the translational level, expression of any of the genes described herein can be measured using immunoassays including immunohistochemical staining, western blotting, ELISA and the like with an antibody that selectively binds to the corresponding gene or a fragment thereof. Detection of the protein using protein-specific antibodies in immunoassays is known in the art. At the transcriptional level, mRNA can be detected by, for example, amplification (e.g., PCR, LCR), or hybridization assays (e.g., northern hybridization, RNAse protection, or dot blotting). The level of protein or mRNA can be detected, for example, by using directly or indirectly labeled detection agents (e.g., fluorescently or radioactively labeled nucleic acids, radioactively or enzymatically labeled antibodies). Changes (e.g., increase or decrease) in the transcriptional levels can also be measured using promoter-reporter gene fusion constructs. For example, the promoter region of a gene encoding any of the genes disclosed herein can be fused (i.e., operably linked) to the coding sequence of a polypeptide that produces a detectable signal. Reporter constructs are well known in the art. Examples of reporter sequences include fluorescent proteins (e.g., green, red, yellow), phosphorescent proteins (e.g, luciferase), antibiotic resistance proteins (e.g., beta lactamase), enzymes (e.g., alkaline phosphatase).

EXAMPLES

Example 1: Differential Gene Expression Analysis

To identify differentially expressed genes the following methods were carried out.

Patients.

Samples were obtained from patients visiting University of Utah Health Care and George Whalen Veterans Affairs Medical Center, Salt Lake City, Utah between age 45 and 75 for routine screening, surveillance or diagnostic colonoscopy. Patients with serrated polyposis syndrome were between 18 to 75 years of age. Subjects with a family history of colon cancer, familial cancers including familial adenomatous polyposis and Lynch syndrome, history of inflammatory bowel disease and prior colonic resections, were excluded. The samples were prospectively collected from 2008-2013 for RNA sequencing. If polyps were found during colonoscopy, a biopsy of polyp tissue was collected in formalin for histopathological diagnosis. If additional polyp tissue remained, a small biopsy of polyp tissue was collected in RNAlater for RNA sequencing. If a polyp was too small to obtain a biopsy for both histology and RNA sequencing (RNA-Seq), a tissue sample for RNA-Seq was not collected for the study.

Twelve sessile serrated polyps were obtained from eight patients with serrated polyposis syndrome (ten right colon and two left colon) (23). SSA/Ps from these patients were previously analyzed for specific mRNA changes by qPCR but not analyzed by RNA sequencing. Uninvolved mucosa from right and left colon was also collected. Right colon was defined as colonic region from splenic flexure to cecum.

Sporadic sessile serrated polyps (n=9, six right colon, three left colon), hyperplastic polyps (n=10, two right colon, eight left colon) and adenomatous polyps (n=10, nine right colon, one left colon) were obtained along with uninvolved mucosa from patients undergoing routine colonoscopy. Normal colon tissue (n=20, ten right colon, ten left colon) was obtained from patients undergoing screening colonoscopy with no polyps found on exam. All samples were collected prospectively and placed in RNAlater (Invitrogen) immediately after tissue removal, stored at 4° C. overnight and then at −80° C. prior to performing RNA isolation. The demographics of sporadic SSA/Ps and hyperplastic polyps are presented in Tables 1 and 2, respectively. The demographics of patients with adenoma and control colon tissues (analyzed using qPCR) have been described previously (23). Four retrospectively obtained frozen colon cancer samples (three right colon, one left colon) obtained from the University of Utah tissue bank were also sequenced.

TABLE 1

Patient demographics with sporadic SSA/Ps.

| Polyp # | Sex | Age | Smoking | BMI | Aspirin | Location | Size (mm) | Adenoma |
|---|---|---|---|---|---|---|---|---|
| 1 | M | 65 | No | 20.5 | No | AC | 7 | No |
| 2 | M | 61 | No | 31 | Yes | Cecum | 18 | No |
| 3 | M | 58 | No | 21 | No | AC | 8 | No |
| 4 | M | 64 | No | 25 | Yes | Rectum | 3 | No |

TABLE 1-continued

Patient demographics with sporadic SSA/Ps.

| Polyp # | Sex | Age | Smoking | BMI | Aspirin | Location | Size (mm) | Adenoma |
|---|---|---|---|---|---|---|---|---|
| 5 | M | 73 | Ex-Smoker | 34.3 | Yes | AC | 7 | No |
| 6 | F | 51 | Ex-smoker | 28.9 | No | SC | 4 | Yes |
| 7 | M | 68 | No | 24 | No | TC | 4 | No |
| 8 | F | 67 | No | 26.9 | No | Cecum | 6 | No |
| 9 | F | 67 | No | 26.9 | No | Cecum | 11 | No |

Demographics of patients with sporadic SSA/Ps and their history of smoking and aspirin intake (n = 9 SSA/Ps from 8 patients, specimens 8 and 9 were obtained from the same patient).
One SSA/P (#6) was from a patient with a concomitant adenoma. AC = Ascending colon, TC = Transverse colon, SC = Sigmoid colon.

TABLE 2

Patient demographics with hyperplastic polyps.

| Polyp # | Sex | Age | Smoking | BMI | Aspirin | Location | Size (mm) | Adenoma | SSA/P |
|---|---|---|---|---|---|---|---|---|---|
| 1 | M | 66 | No | 30.4 | Yes | SC | 5 | Yes | No |
| 2 | M | 56 | No | 32.9 | No | SC | 4 | No | No |
| 3 | M | 49 | Ex-smoker | 39 | No | SC | 4 | Yes | No |
| 4 | M | 64 | Ex-smoker | 27.2 | No | HF | 5 | Yes | No |
| 5 | M | 64 | Ex-smoker | 27.2 | No | Rectum | 5 | Yes | No |
| 6 | M | 59 | No | 32.4 | No | Rectum | 5 | Yes | No |
| 7 | M | 64 | Yes | 29 | Yes | SC | 5 | No | No |
| 8 | M | 64 | Yes | 29 | Yes | Rectum | 5 | No | No |
| 9 | M | 64 | No | 25 | Yes | SC | 5 | No | Yes |
| 10 | F | 57 | No | 19 | No | SF | 7 | No | No |

Demographics of patients with hyperplastic polyps (HPs) and their history of smoking, aspirin intake and concomitant adenoma or SSA/P on exam (n = 10 HPs from 8 patients, polyps 4-5 and 7-8 were each from a single patient) HF = Hepatic flexure and SF = Splenic flexure.

Pathological Classification.

All biopsy specimens were reviewed by an expert GI pathologist. Serrated polyps were classified according to the recent recommendations of the Multi-Society Task Force on Colorectal Cancer for post-polypectomy surveillance and as described previously (23, 24). Hyperplastic polyps were not subdivided into microvesicular hyperplastic polyps (MVHP) and goblet cell hyperplastic polyps (GCHP) since these classifications are not used clinically or discussed in the recent post-polypectomy colonoscopy surveillance guidelines (24). The classification followed herein is most appropriate and practical in clinical practice with the aim to define clinically relevant and realistic gene signatures. Moreover, these two HP subtypes have not been shown to have different risks for development of colon cancer.

RNA Isolation.

RNA was isolated using TRIzol (Invitrogen) as described previously (23, 25, 26). The quantity of total RNA (10-25 µg) was determined by NanoDrop spectrophotometry and RNA quality was assessed by Agilent 2100 Bioanalyzer analysis. Samples with RNA integrity number (RIN) ≥7 were used for gene expression analyses.

RNA Sequencing, Differential Expression Analysis and Statistical Analysis.

RNA sequencing was performed on 86 individual colon samples: 21 SSA/Ps (12 syndromic and 9 sporadic), 10 hyperplastic polyps, 10 adenomatous polyps, 21 uninvolved colon, 20 control colon, and 4 colon cancer samples. PCR amplified cDNA sequencing libraries were prepared using oligo dT-selected RNA according to the Illumina TruSeq library protocol. Illumina single-end 50 bp sequence reads were aligned to the GRCh37/Hg37 human reference genome using the novoalign application (Novocraft) as described previously (23). The USeq DefineRegionsDifferentialSeq (DRDS) application was used to count the reads intersecting exons of each annotated gene and score them for differential expression between polyp subtypes and normal colon using DEseq2 negative binomial statistics (28). Hierarchical clustering of differentially expressed genes was performed using Cluster 3.0 and Java Treeview software as described previously (23).

Results.

Figure 1B:
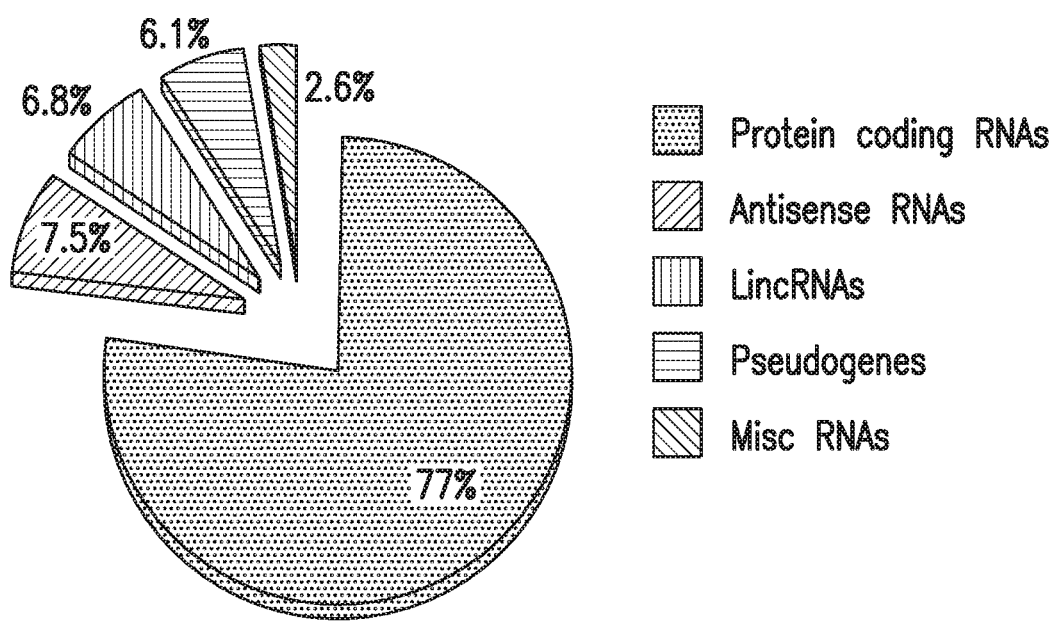

RNA sequencing was performed on 86 colon specimens with a mean sequence depth of 14.7 million mapped reads per sample. Comparing syndromic (n=12) and sporadic (n=9) SSA/P RNA-seq datasets to control right (colon (n=10)), 1422 differentially expressed annotated genes (≥2-fold change, FDR<0.05) were identified by negative binomial statistical analysis (FIG. 1A). Comparing hyperplastic polyps (HPs, n=10) to control (left colon (n=10)), 711 differentially expressed genes were identified using the same fold change and FDR cutoff 475 genes were differentially expressed in both SSA/Ps and HPs. In the RNAs that were differentially expressed in SSA/Ps, 1095 (77%) were protein coding and 327 (23%) were non-coding (FIG. 1B). A similar percentage of protein coding (80%) and non-coding (20%) RNAs was also significantly differentially expressed in HPs relative to control colon.

Figure 2A:
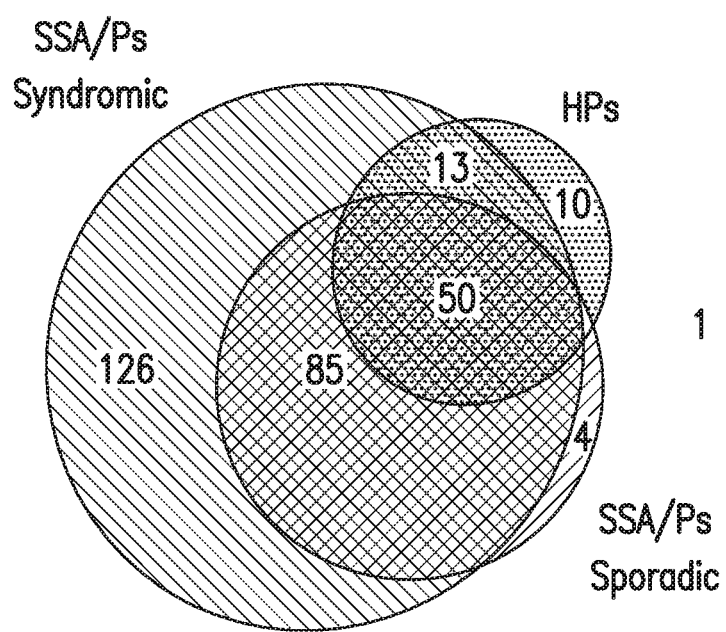
FIG. 2A-C shows differentially expressed genes in syndromic and sporadic SSA/Ps and HPs by RNA sequencing.
Figure 5:
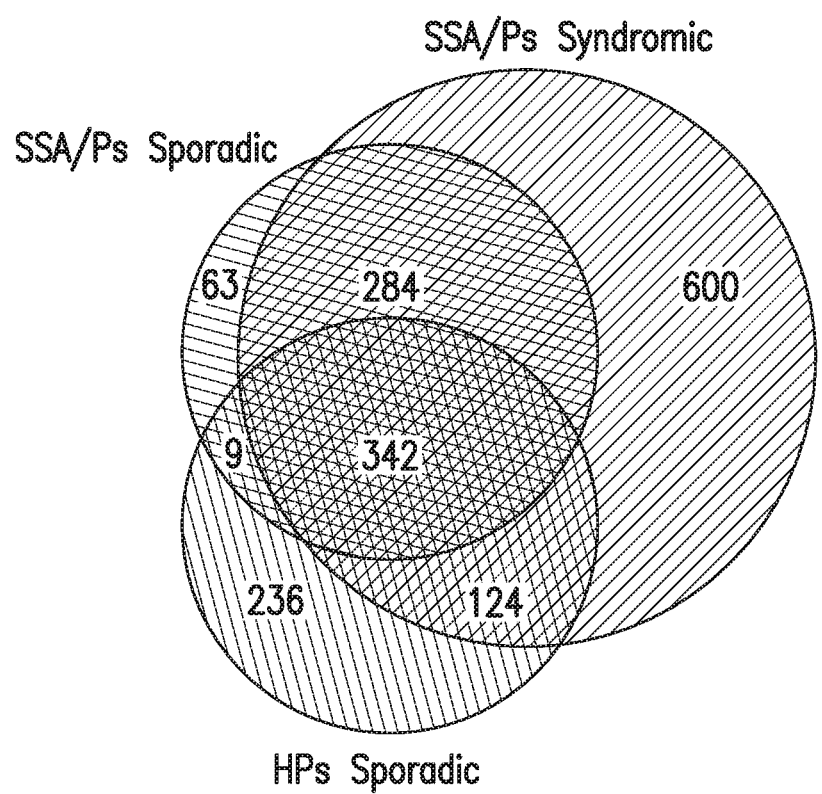
FIG. 5 illustrates genes differentially expressed with ≥2-fold in syndromic and sporadic SSA/Ps and hyperplastic polyps by RNA sequencing.

To determine if sporadic SSA/Ps had a gene expression profile similar to syndromic SSA/Ps, differentially expressed genes were compared with a ≥2- and 4-fold change in each group (FIG. 5 and FIG. 2A, respectively). Differentially expressed genes with ≥2-fold change and FDR<0.05 in syndromic SSA/Ps (n=12), sporadic SSA/Ps (n=9) and HPs (n=10) were compared to control colon. Syndromic and sporadic SSA/Ps were compared to control right colon (n=10) and HPs were compared to control left colon (n=10). 1350, 698 and 711 genes were differentially expressed in syndromic and sporadic SSA/Ps and HPs, respectively. 1422 genes in total were differentially expressed in either syndromic or sporadic SSA/Ps.

Figure 2B:
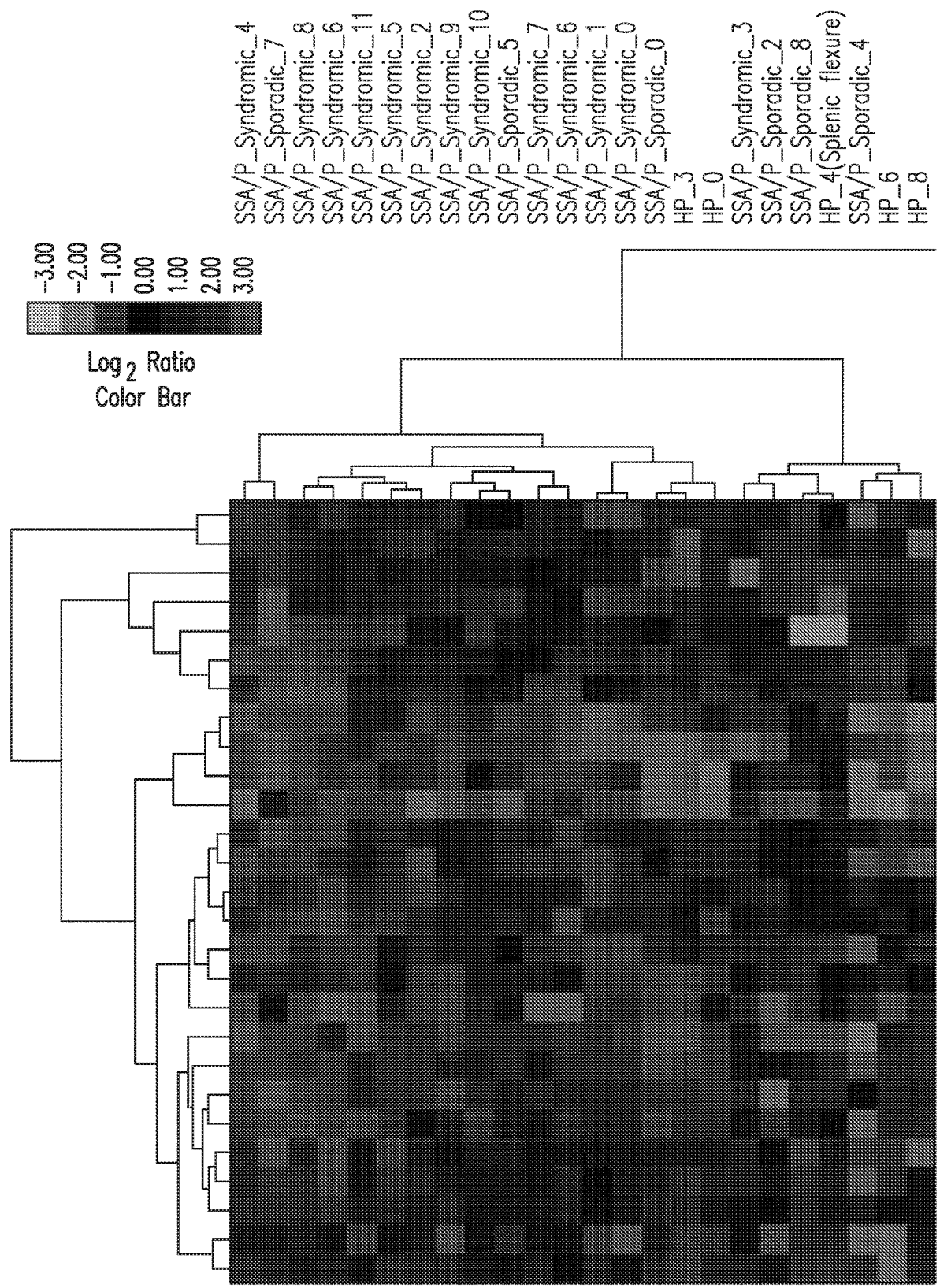
Figure 2B:
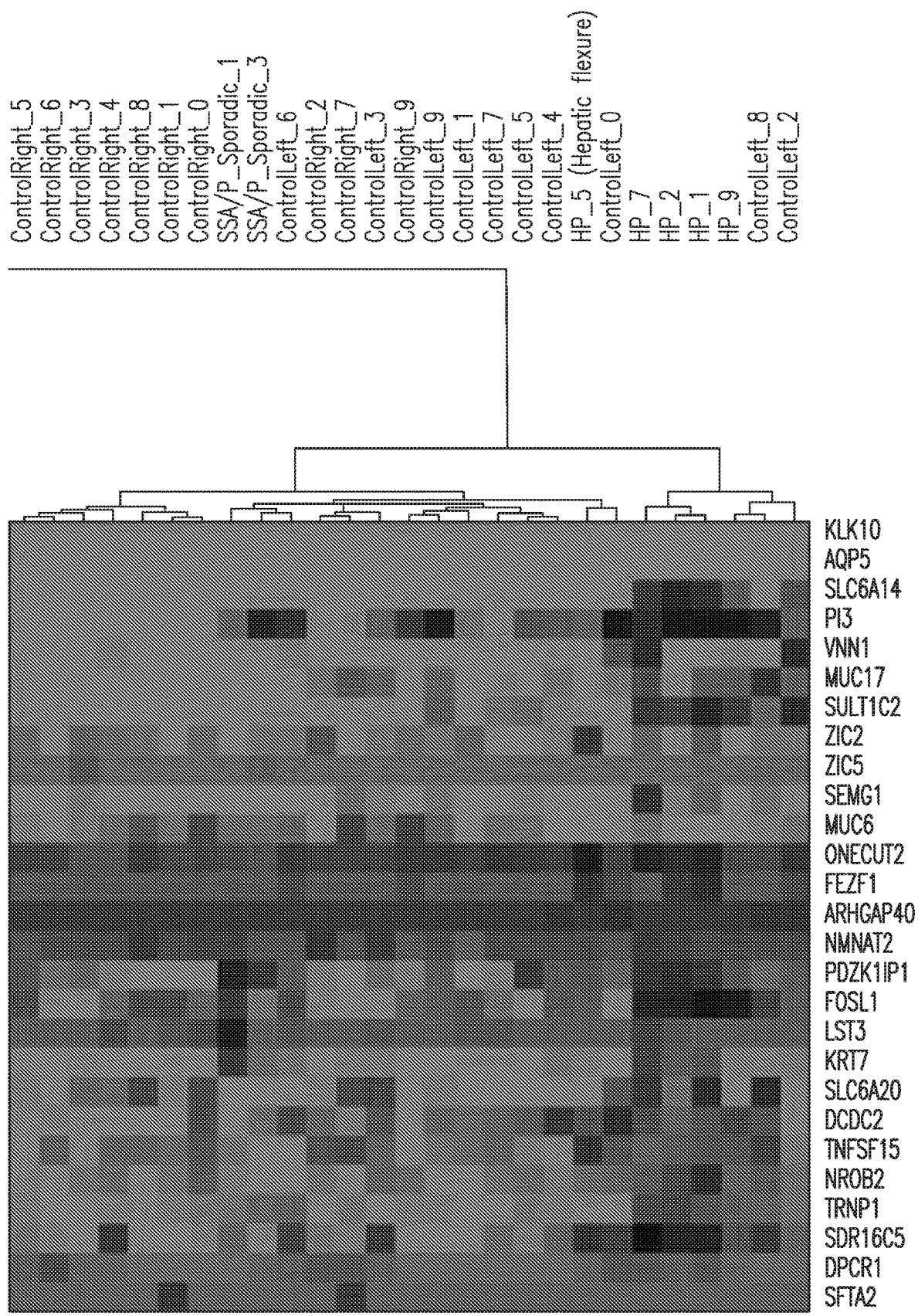
Figure 2C:
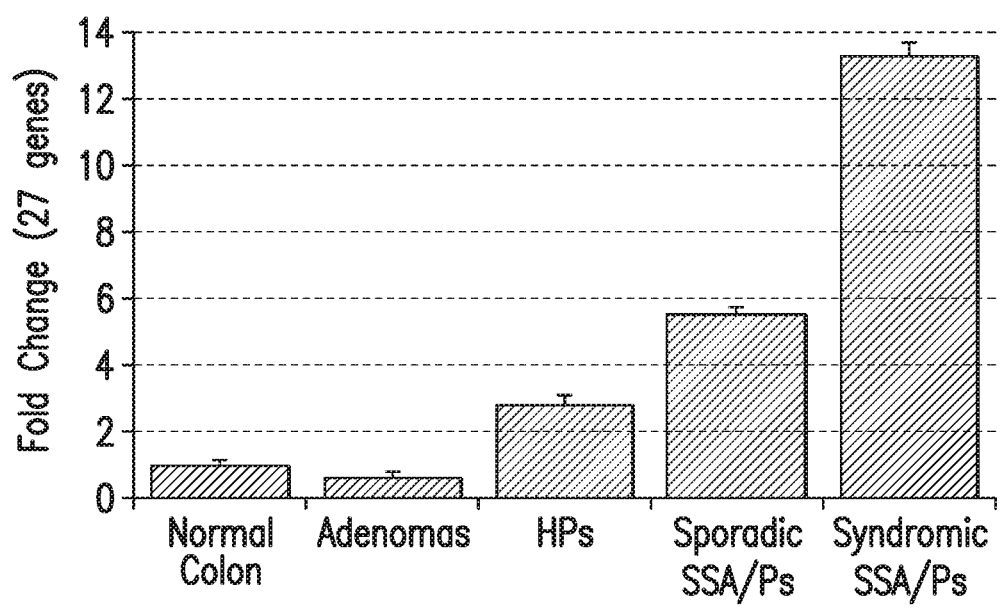

Greater than 89% (≥2 fold) and 96% (≥4 fold) of the differentially expressed genes observed in sporadic SSA/Ps were also differentially expressed in syndromic SSA/Ps. Another gene expression comparison of sporadic and syndromic SSA/Ps has not been reported in the literature, and thus, these results describe major molecular similarities in SSA/Ps from these two very different patient cohorts. 215 genes (77%) were uniquely differentially expressed ≥4-fold in SSA/Ps as compared to HPs (FIG. 2A) while nearly 86% of the differentially expressed genes in HPs overlapped with SSA/Ps and only 10 genes (14%) were uniquely differentially expressed ≥4-fold in HPs. These findings suggest that the molecular phenotype in HPs (considered at little or no risk for progression to colon cancer) is surprisingly similar to that of SSA/Ps (considered high risk). One notable difference between SSA/Ps and HPs was the magnitude of fold-change in many differentially expressed genes. Hierarchical clustering of 27 protein-coding genes with average increased expression >13 fold in SSA/Ps illustrates what was shared in gene expression changes among all but two of the SSA/Ps (FIG. 2B). It should be noted that 2/10 (20%) HPs and 5/21 (24%) SSA/Ps were from right and left colon, respectively. Although the numbers of HPs from right colon and SSA/Ps from left colon are small, appreciable differences in gene expression between left and right HPs or SSA/Ps were not observed. Increased expression of these 27 genes was not observed in adenomatous polyp RNA-seq datasets (FIG. 2C).

Figure 6:
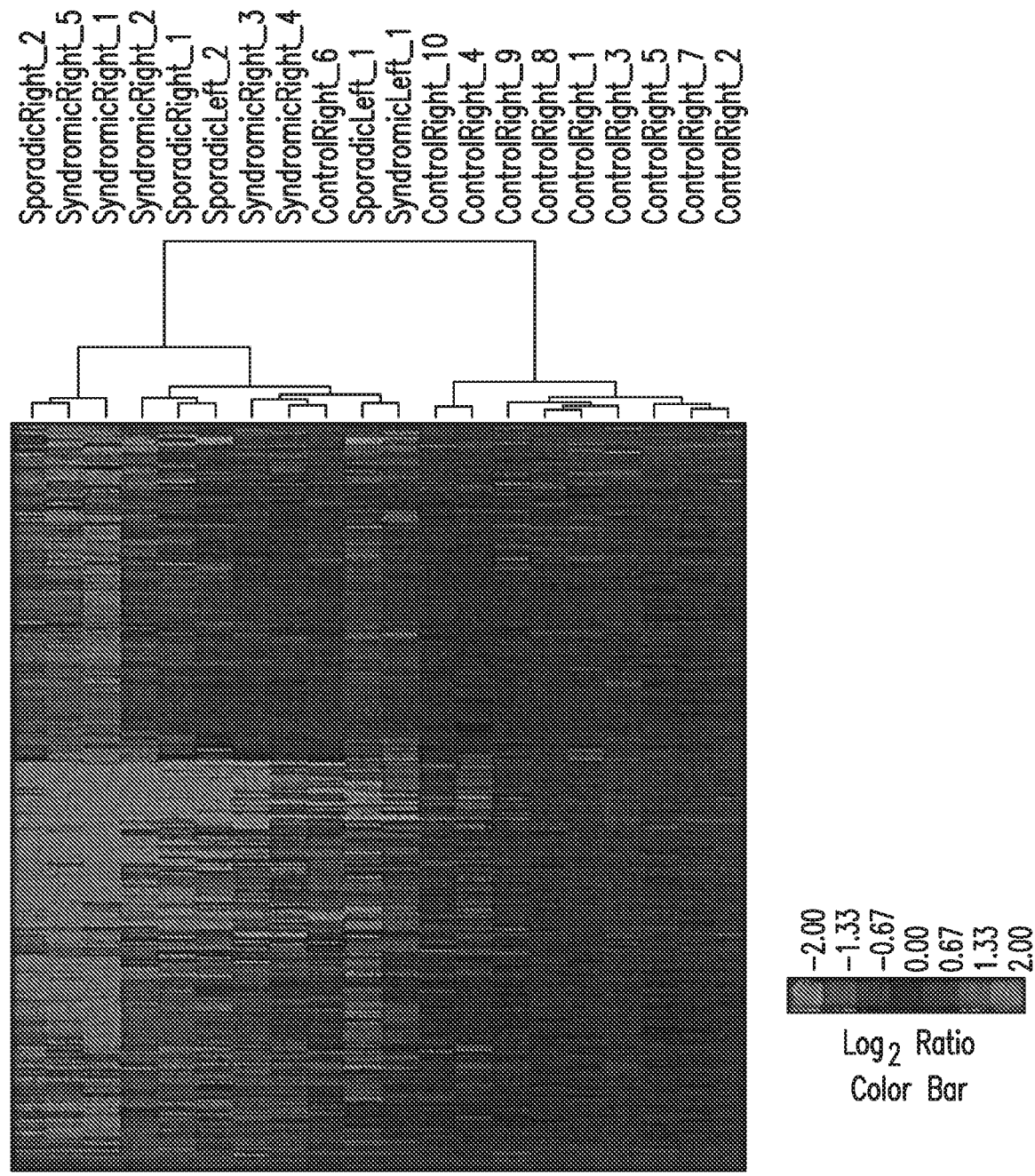
FIG. 6 shows the comparison of gene expression in uninvolved colon from patients with SSA/Ps with control colon from patients without polyps.

Next, gene expression in the uninvolved colon (n=10) of serrated polyposis syndrome (SPS) patients and patients with sporadic SSA/Ps were compared with the control right colon (n=10) of patients undergoing screening colonoscopy with no polyps (FIG. 6). Surprisingly, 1922 genes were differentially expressed (≥2-fold change, FDR<0.01) between the uninvolved colon of patients (n=10, 7 right and 3 left) with SSA/Ps and control colon (n=10). Uninvolved colon includes six uninvolved colon from syndromic patients with SSA/Ps and four uninvolved colon from sporadic patients with SSA/Ps. $\log_e$ ratios comparing each individual sample to the mean of 10 right control colon samples was used for hierarchical clustering. A significant overlap in the gene expression profile of uninvolved colon from patients with SPS and sporadic SSA/Ps was observed. The magnitude of fold change, however, was small for most genes (<3 fold) and the genes differentially expressed were not common to genes differentially expressed in SSA/Ps.

A significant number of the genes that were differently expressed in the uninvolved colonic mucosa of patients with syndromic (SPS) and sporadic SSA/Ps, relative to normal colon (patients with no polyps), overlapped and suggest a field effect may be present in the colonic mucosa of patients with SSA/Ps. These genes were different from those found common to syndromic and sporadic SSA/Ps and had smaller fold changes relative to controls. A 'field cancerization' effect has been reported in studies of sporadic colon cancer (57, 58). Few studies have investigated possible field effects in patients with colon polyps, particularly SSA/Ps (59). The results presented herein raise important questions regarding the origin of such changes.

Comparing the transcriptome of SSA/Ps and HPs produced findings that raise some critical questions about these two subtypes of serrated polyps with different potentials for progression to colon cancer. It is unclear if serrated adenocarcinoma originates directly through SSA/Ps or if genetic alterations in certain hyperplastic polyps found in right colon lead to the development of SSA/Ps and eventually to colon cancer. SSA/Ps, especially in the serrated polyposis syndrome, have a significant risk for progression to cancer (9-11) whereas HPs have a negligible risk (38, 39). The finding that most of the genes found differentially expressed in HPs were also found in SSA/Ps at least partly explains why both types of polyps have a similar morphological appearance. On the other hand, there were many differentially expressed genes in SSA/Ps compared to HPs. The SSA/Ps gene signature established in this study provides an opportunity to identify critical pathways that may explain these differences in cancer risk.

A limitations of the study described herein includes a small sample size in each individual patient cohort (n=9 to 12). This is, in part, due to colon biopsies being collected prospectively and the low prevalence of sporadic SSA/Ps and the serrated polyposis syndrome in the general population. Even with this limitation, the results described herein are the largest RNA-sequencing study performed to characterize the transcriptome of SSA/Ps. Finally, the gene panel disclosed herein was not validated in a separate RNA-Seq study of serrated polyps because these datasets are not publically available. The gene signature disclosed herein, however, did accurately classify SSA/Ps from MVHPs using expression data from a previous microarray study.

Example 2: Selection and Cross Validation of a Gene Signature that Differentiates SSA/Ps from HPs Sequencing data from 10 HP and 21 SSA/Ps samples were used to construct and cross validate a gene signature. Prior to analysis, genes differentially expressed between left and right colon (≥2-fold change, false discovery rate (FDR) <0.01) were removed. An "unpaired" analysis was then performed on all 31 serrated polyp samples using DESeq2 negative binomial statistics with histology as the only predictor. The FDR threshold for the signature genes was set at 0.01. Twenty eight genes met these criteria and were used for cross validation. The average of log (count+0.5) for the selected genes was used to form separate signatures for HP and SSP samples. A normalized Euclidean distance measure was constructed from the selected genes. Standard deviations <0.05 were increased to 0.05 in the normalization so that genes with unrealistically low variability did not exert excess influence on the signature (30). The signature for each class is represented by the geometric average, or centroid, of the class. Samples are predicted to be in the class with the closest centroid. In order to evaluate the signature, the entire process of selection of the genes to form the signature, construction of the centroid for each class, calculation of the Euclidean distance measure and classification, was cross-validated. A principal component analysis was performed using Cluster 3.0 and a 3D plot constructed using the 'rgl' package in R.

Figure 3A:
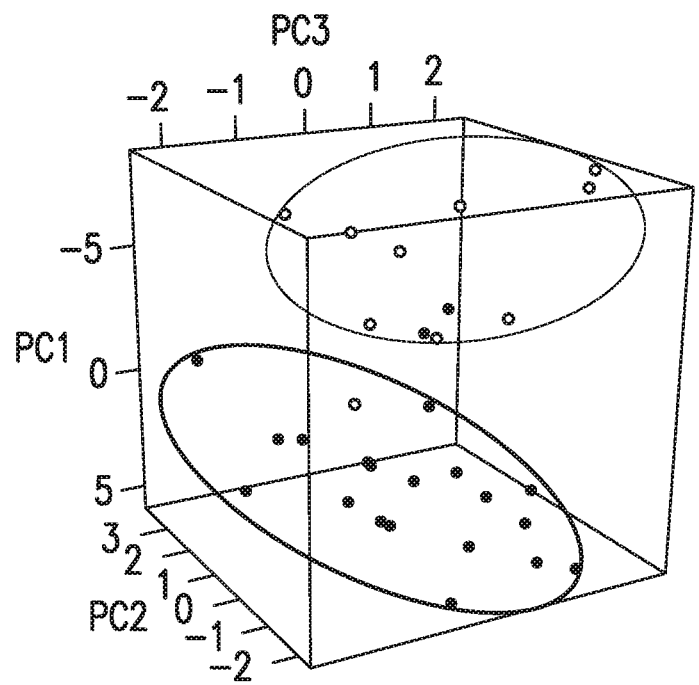
FIG. 3A-B shows the results of an evaluation of a 28-gene signature to distinguish SSA/Ps from HPs. The 28-gene panel was developed using a leave-one-out cross validation approach on 31 independent serrated polyp (21 SSA/Ps and 10 HPs) samples.
Figure 3B:
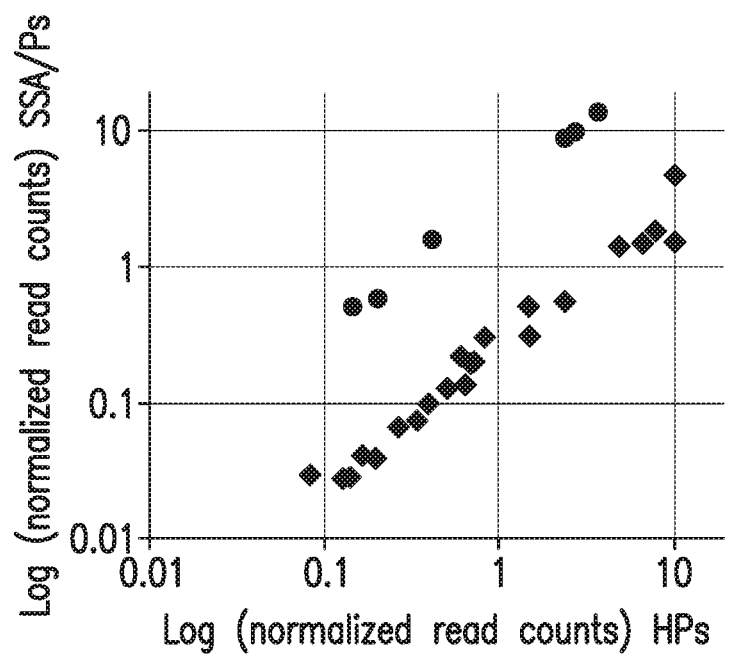

Count data from 31 serrated polyps (21 SSA/Ps and 10 HPs) were used in a leave-one-out cross-validation analysis. Twenty-eight genes with an FDR<0.01 and ≥2-fold change (SSA/Ps vs HPs) defined the signature. Twenty-eight of 31 serrated polyps were classified correctly for a nominal error rate of 10%. After cross validating four times, the cross-validated error rate was 18%. Principal component analysis of the gene expression of each of the 28 genes in all 31 serrated polyps is shown in FIG. 3A that demonstrates the misclassification of two SSA/Ps and one HP. The relative expression of each of the 28 genes in SSA/Ps and HPs is shown in FIG. 3B. Six genes were overexpressed and twenty-two underexpressed in SSA/Ps relative to HPs.

Example 3: Evaluation of Gene Signature in Published Microarray Data of Serrated Polyps For the analysis of signature genes in published microarray data of serrated polyps, no previously published RNA-Seq data of serrated polyps was available for comparison to the datasets described herein. The expression of each of the 51 signature genes described herein and in a previously published microarray dataset (GEO number GSE43841) (21) were evaluated.

For this analysis, quantile normalized expression data for each signature gene was downloaded from the Gene Expression Omnibus (GEO) under accession number GSE43841. Expression data from six SSA/Ps, six MVHPs and six control colon FFPE samples (three right and three left) was evaluated for expression of our gene markers. Hierarchical clustering of $\log_2$ ratio values comparing each individual colon sample (SSA/P—sessile serrated adenoma/polyp, MVHP—microvesicular hyperplastic polyp, CTRL—control colon) to the mean of all 18 colon samples is shown. Red and green denote overexpression and underexpression, respectively. Clustering was performed using a correlation metric and complete linkage.

Results.

Figure 7:
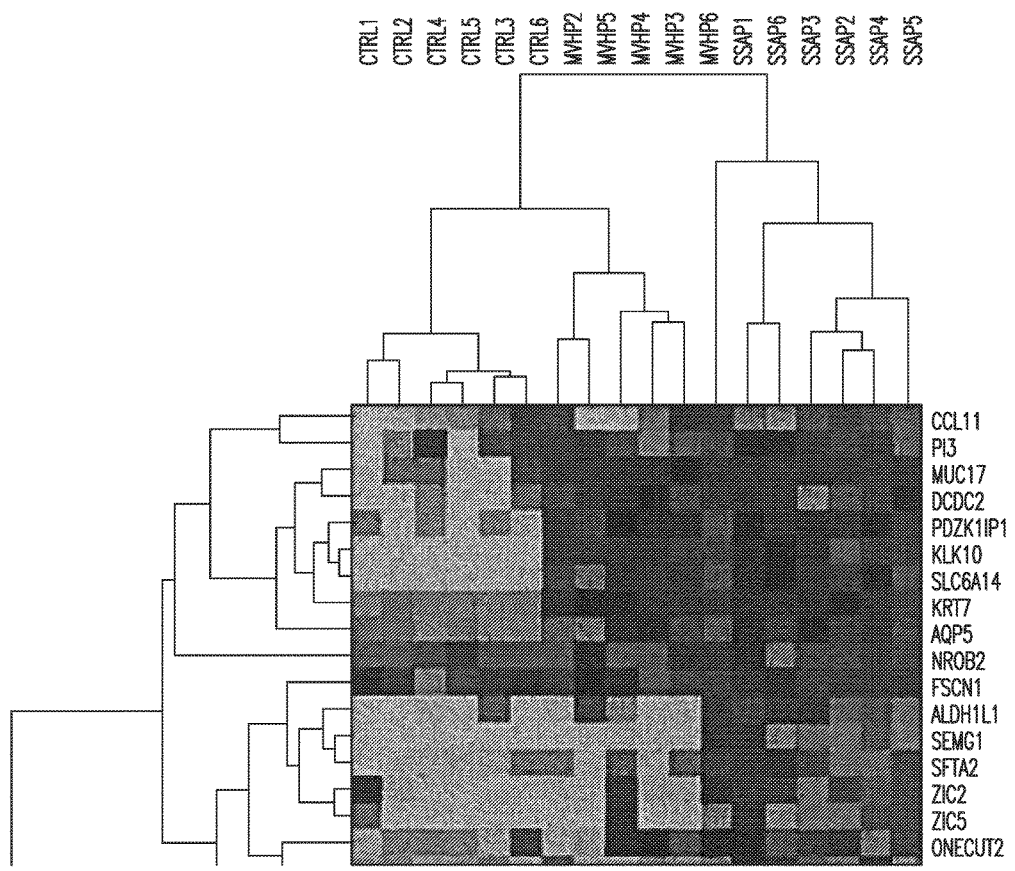
FIG. 7 shows the results of an evaluation of an SSA/P gene signature using previously published microarray data of SSA/Ps, MVHPs and control colon. Expression data from six SSA/Ps, six MVHPs and six control colon FFPE samples (three right and three left) was evaluated for expression of these gene markers. Hierarchical clustering of $log_2$ ratio values comparing each individual colon sample (SSA/P—sessile serrated adenoma/polyp, MVHP—microvesicular hyperplastic polyp, CTRL—control colon) to the mean of all 18 colon samples is shown. Red and green denote overexpression and underexpression, respectively. Clustering was performed using a correlation metric and complete linkage.
Figure 7:
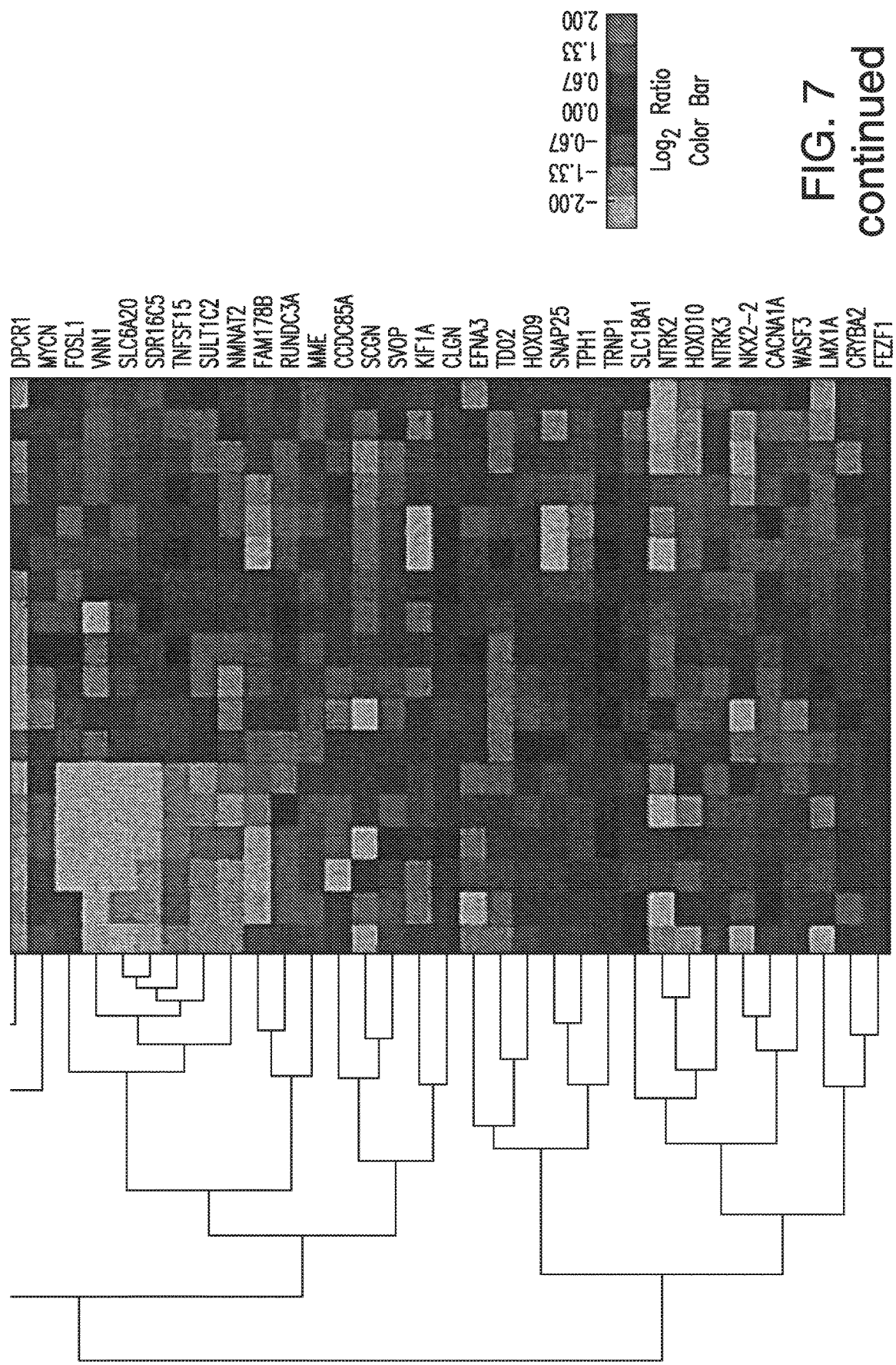

The relative expression of each of the 51-gene signature in SSA/Ps, MVHPs and normal colon (left and right) from a previously published microarray study was compared (21). Clear separation of SSA/Ps from MVHPs and control colon was observed by hierarchical clustering (FIG. 7). In fact, five out of six MVHPs, showed gene expression patterns more closely resembling control colon than SSA/Ps.

Example 4: Identifying Colon Cancers with the SSA/P Gene Signature in the Cancer Genome Atlas Fifty-one SSA/P signature genes were used to interrogate 68 colon cancer RNA-Seq datasets from The Cancer Genome Atlas (TCGA, 36 specimens from Christiana Healthcare and 32 from Memorial Sloan Kettering) and four from the University of Utah (31). Raw sequencing data for each colon cancer dataset was downloaded from the TCGA database (32) and normalized by number of transcript reads per kilobase of gene length per million of total reads (RPKM). There was expression data for 18130 unique RefSeq genes in both the TCGA and University of Utah RNA-Seq datasets. One hundred and ninety-five TCGA colon cancer datasets were evaluated for mRNA expression in the 51 signature genes using the cBioPortal for Cancer Genomics (32, 33). MLH1 methylation data was also evaluated in 30 hypermutated and 165 non-hypermutated and correlated with gene expression data.

Changes in mRNA expression were obtained by comparing normalized read counts (RPKM) for each gene across colon cancers diploid for each gene. Statistically significant differences between incidence of increased mRNA expression between hypermutated and non-hypermutated were determined using a Fisher Exact test. Nine genes showed statistically significant increased incidence of mRNA overexpression in hypermutated colon cancers (FIG. 9).

Normalized RPKM for each of a seven gene panel was downloaded from the cBioPortal for Cancer Genomics using the CGDS-R package http://www.cbioportal.org/cgds_r.jsp. One hundred eighty-six TCGA colon cancers had mRNA expression, BRAF mutation, methylation subtype and MLH1 methylation data available. Thirty one of 186 colon cancers (17%) were BRAF mutated, CIMP-H and/or MLH1 silenced. The majority of these cancers 20/31 (64%) had two or more of these DNA alterations highly suggestive of colon cancers developing via the serrated pathway (FIG. 10).

Incidence of increased mRNA in 195 colon cancers (29 methylated and 166 non-methylated) was obtained using TCGA data available in the cBioPortal for Cancer Genomics, Memorial Sloan-Kettering Cancer Center. 15/51 signature genes show frequent (≥10%) increased mRNA expression in CIMP-H and/or MLH1 silenced colon cancers. Incidence of increased mRNA expression is also shown for two previously developed SSA/P gene markers, annexin A10 (ANXA10) and claudin 1 (CLDN1). Changes in mRNA expression were obtained by comparing normalized read counts for each gene across colon cancers diploid for each gene. Statistically significant differences between the incidence of increased mRNA expression in methylated and non-methylated colon cancers were determined using a Fisher Exact test. Eleven genes showed statistically significant increased incidence of mRNA overexpression in CIMP-H and/or MLH1 silenced colon cancers (FIG. 11).

Results.

Figure 4A:
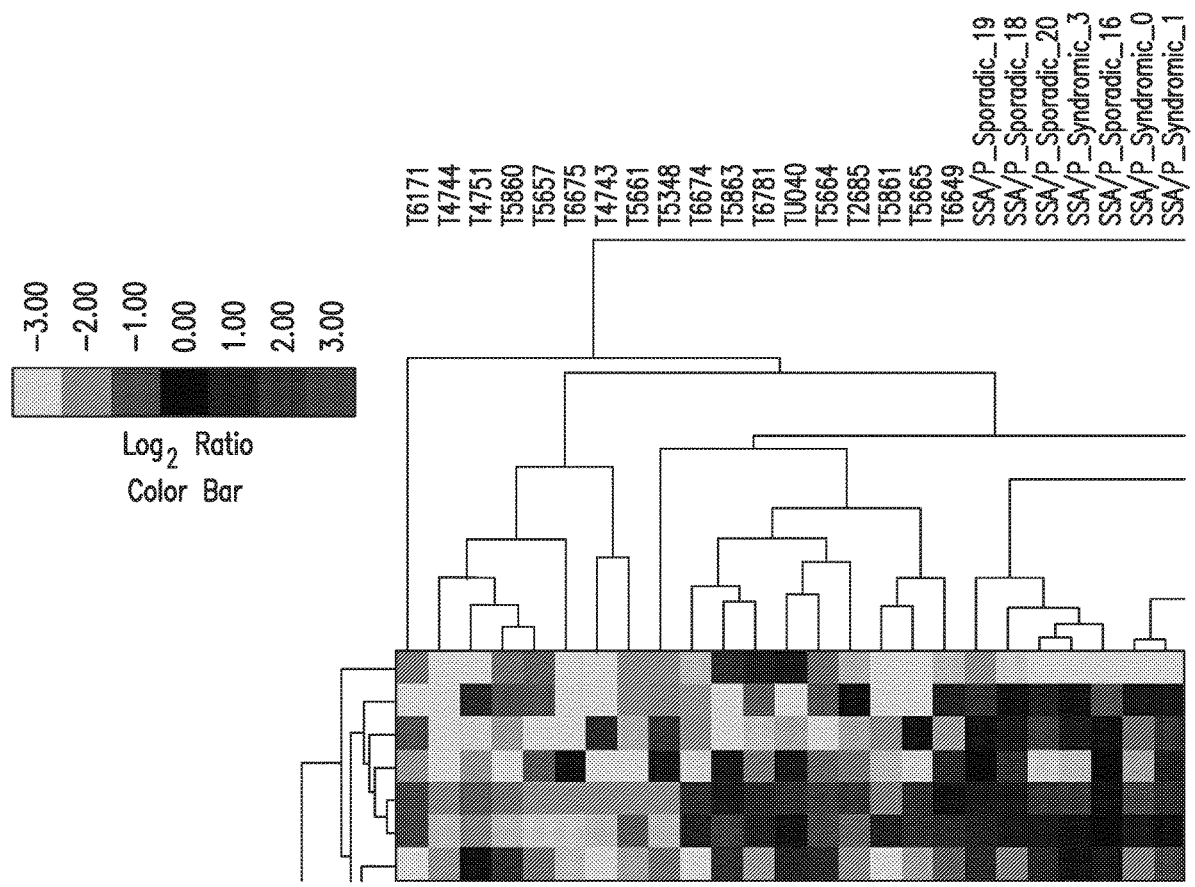
FIG. 4A-B shows the results of an evaluation of a 51 SSA/P gene signature in colon cancer RNA sequencing datasets from The Cancer Genome Atlas (TCGA).
Figure 4A:
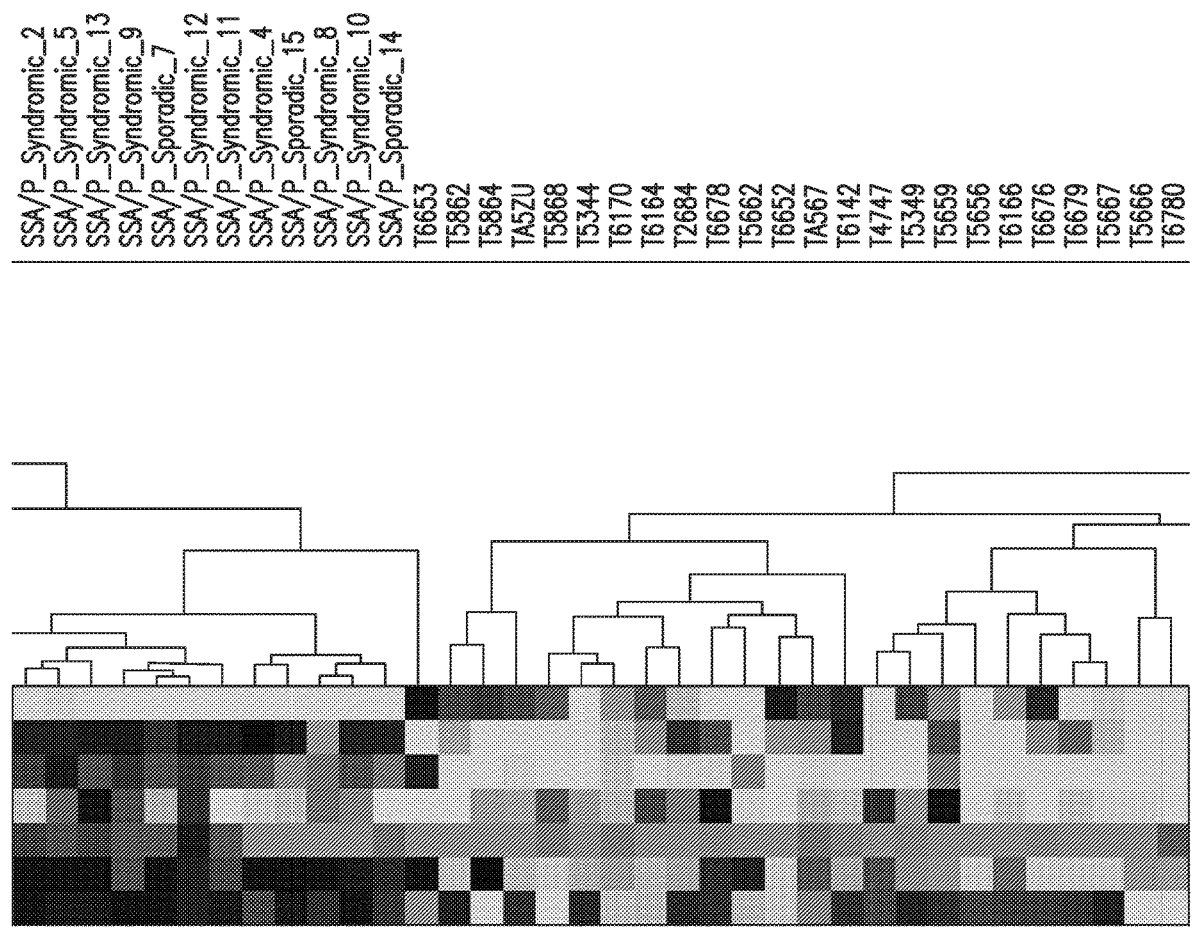
Figure 4A:
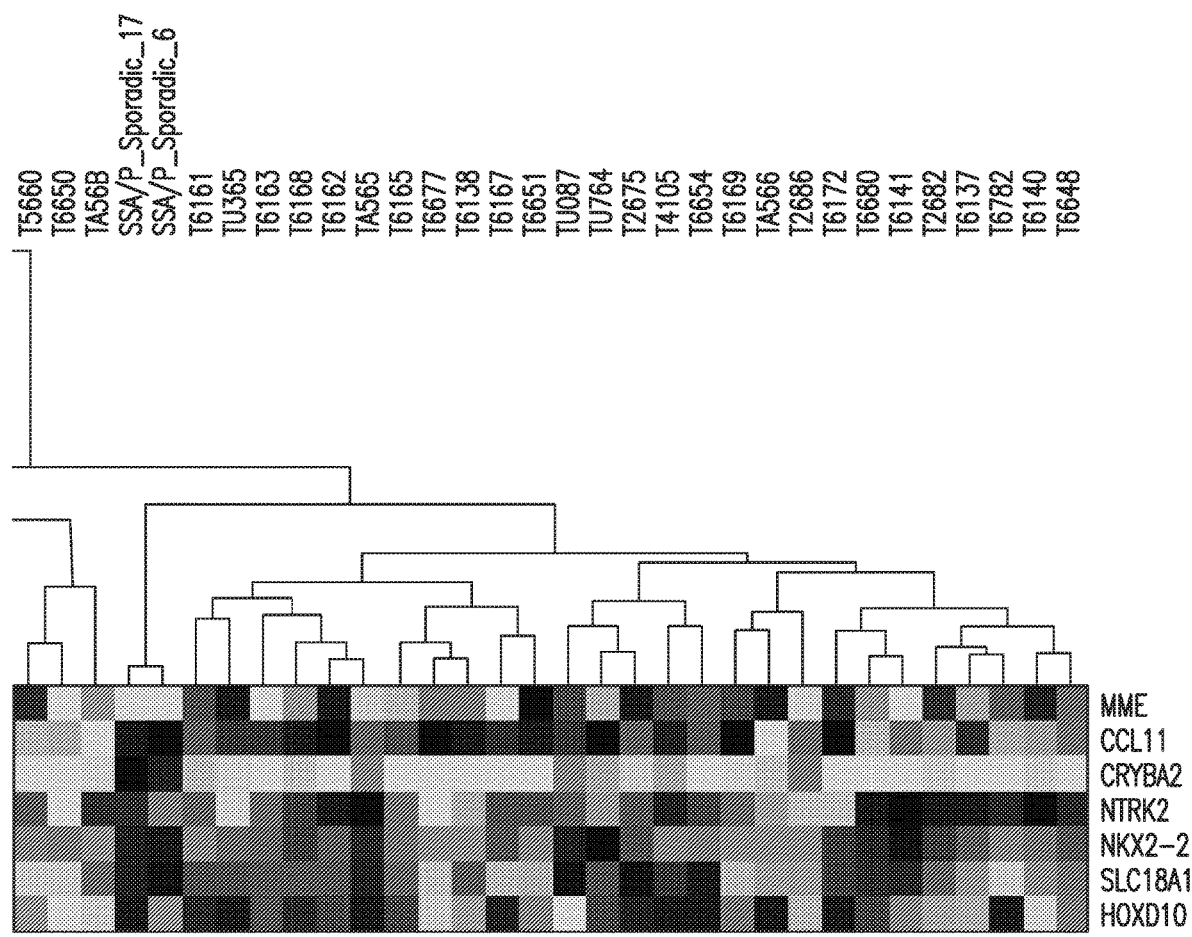
Figure 4A:
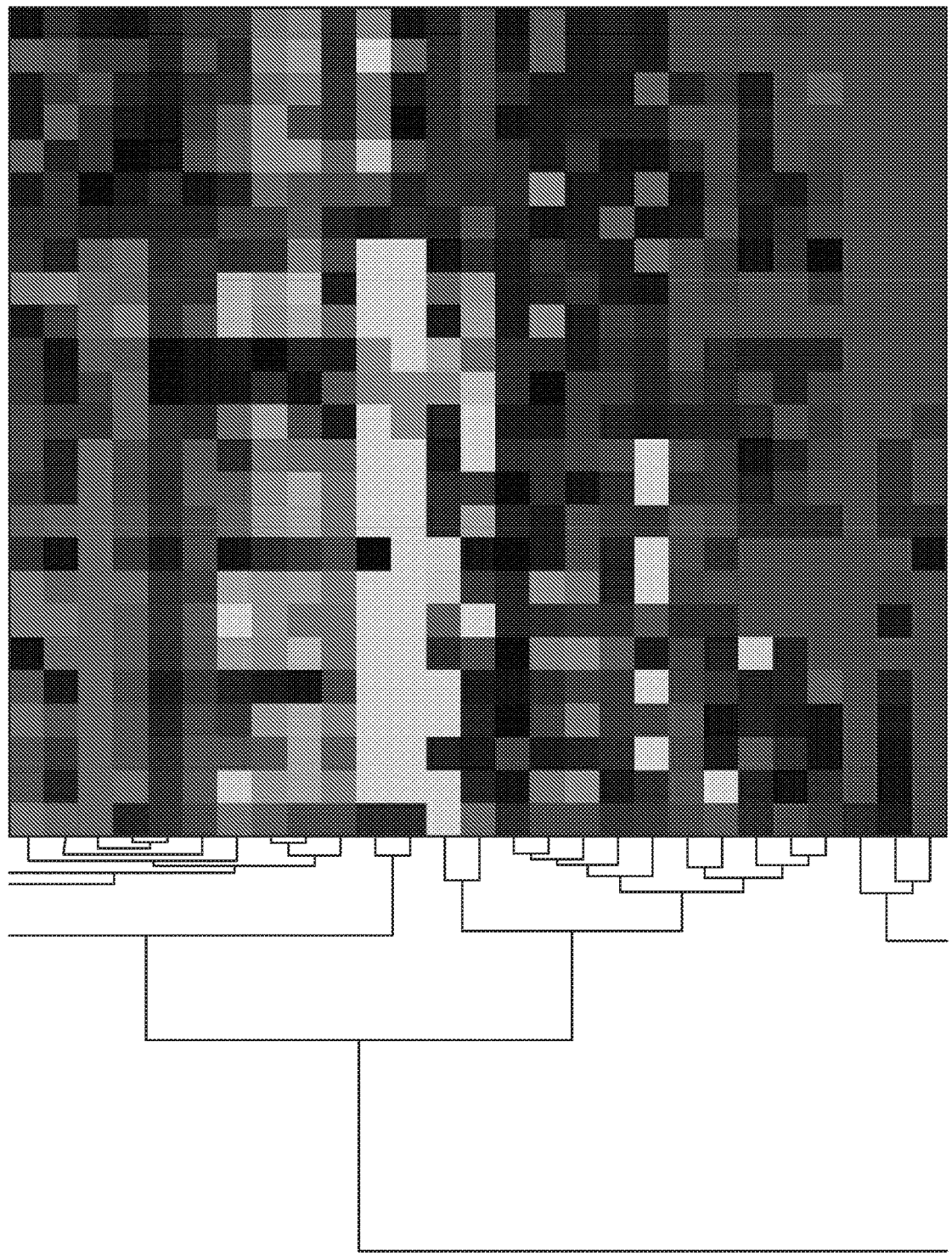
Figure 4A:
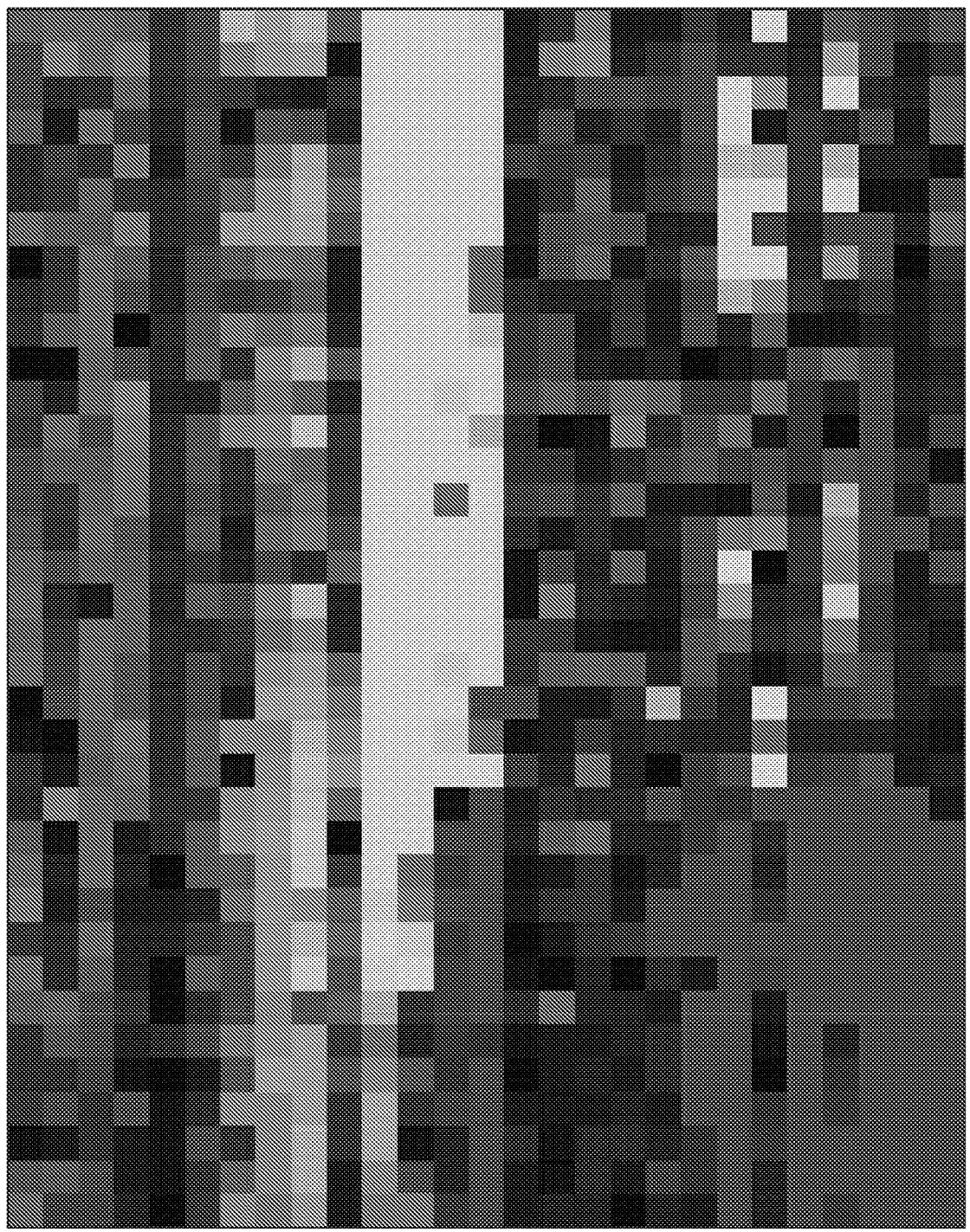
Figure 4A:
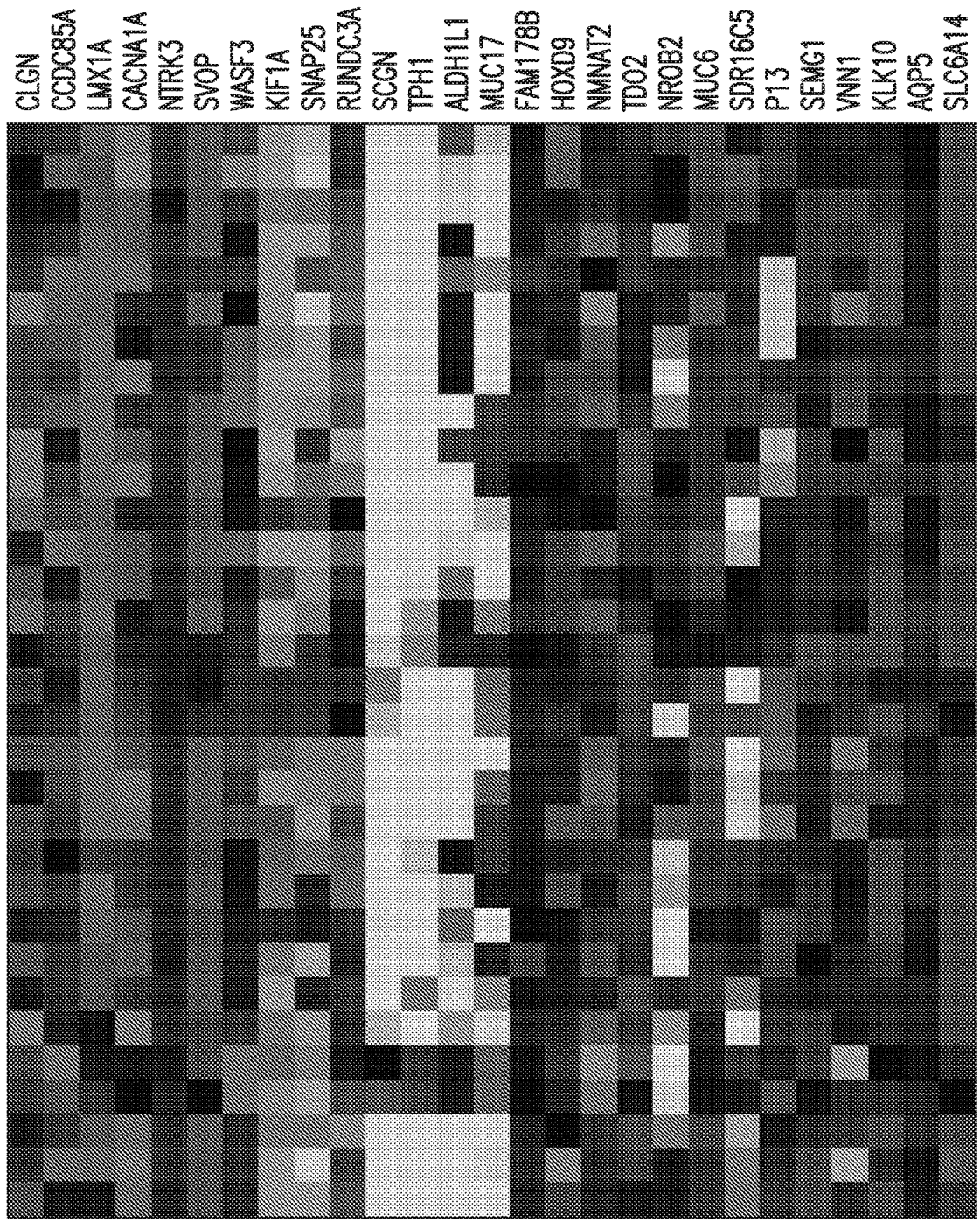
Figure 4A:
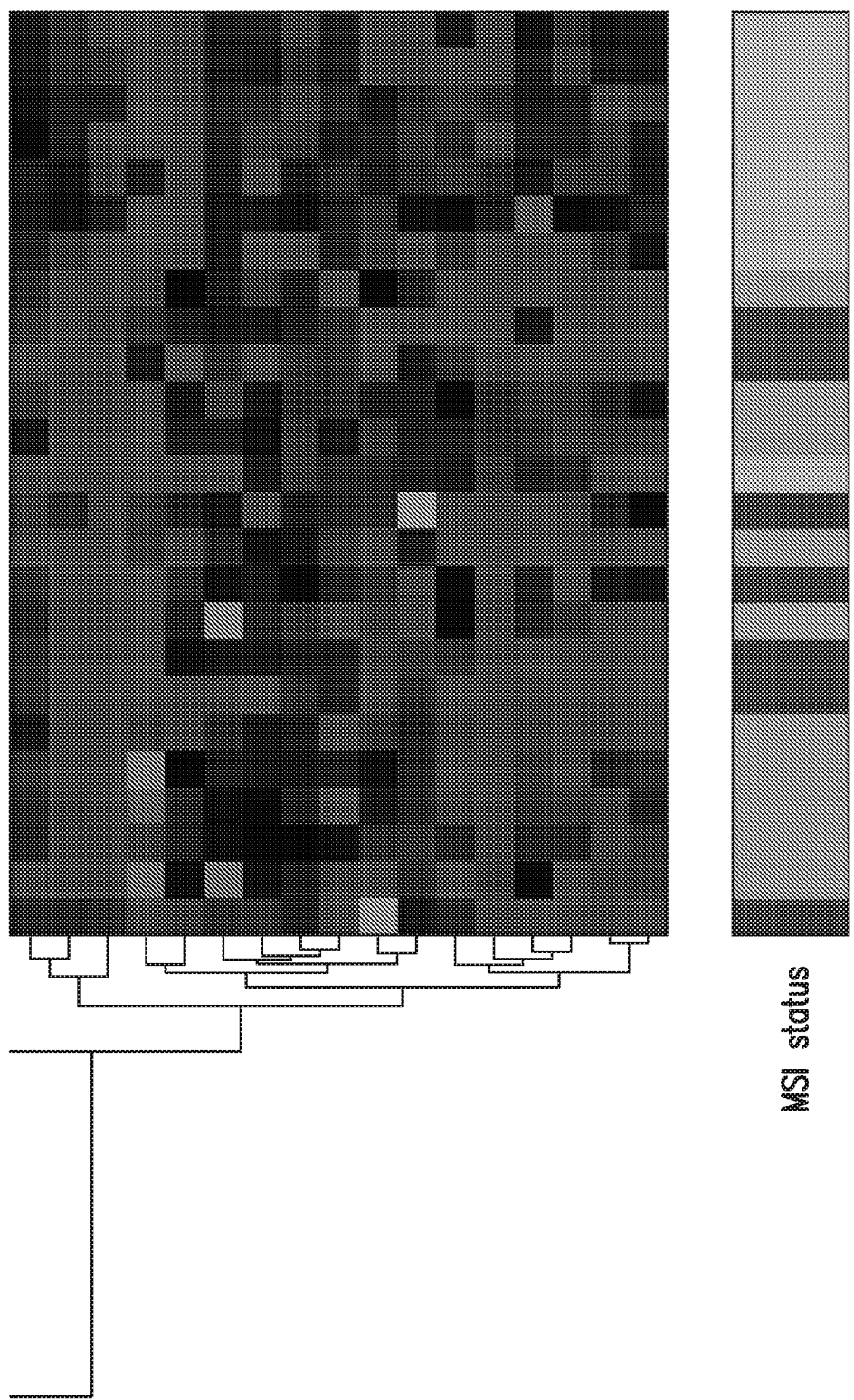
Figure 4B:
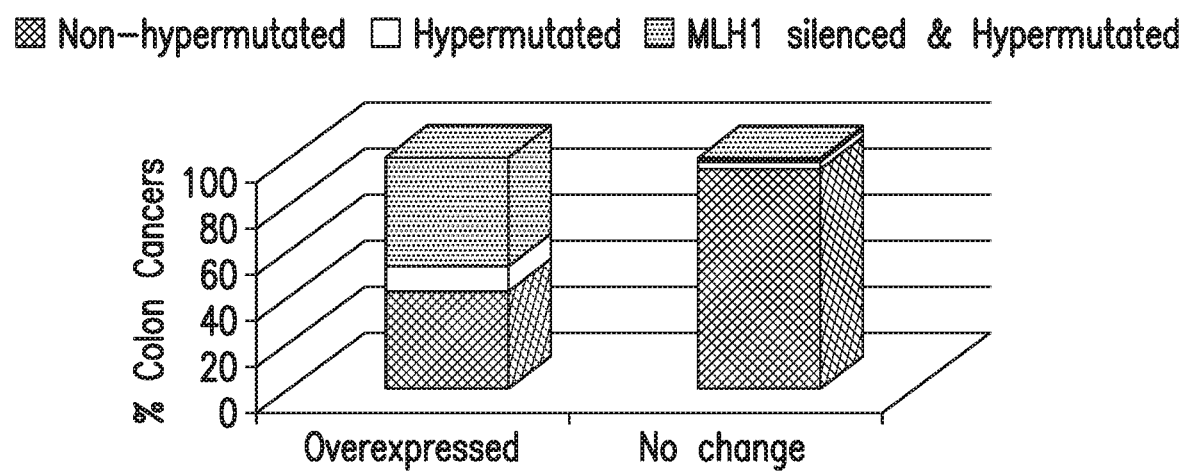

The 51 gene SSA/P signature was compared to the sixty-eight colon cancer RNA-seq datasets available in the Cancer Genome Atlas and four colon cancers obtained from the University of Utah (FIG. 4A). RNA-seq data from 4 of the 55 genes were not available in the TCGA datasets. RNA sequencing was performed on four colon cancers from the University of Utah to identify potential lab/batch effect differences in gene expression between our RNA-Seq datasets and the TCGA datasets. The 51 gene SSA/P signature showed similar expression patterns between syndromic and sporadic SSA/Ps and the MSI-H subset of colon cancers. No batch effects were observed between the colon cancer datasets described herein and the TCGA datasets. Sixty-three out of 72 cancers had data on their MSI status with 11 cancers being MSI-H (MSI status unknown for 9 colon cancers). Eighteen colon cancers clustered with SSA/Ps and 8 of the 18 colon cancers (44%) were MSI-H. This is a significant finding since of the remaining 54 colon cancers that did not cluster with SSA/Ps of which 3 were MSI-H (6%). These data suggests that our SSA/P signature identifies MSI-H cancers.

mRNA expression of each of our 51 SSA/P signature genes in 195 TCGA colon cancers was also evaluated using the cBioPortal for Cancer Genomics. Thirteen of the 51 signature genes had frequent increased mRNA expression in 10% of hypermutated colon cancers but not in non-hypermutated cancers (FIG. 9). Seven of these genes (FSCN1, ZIC2, ZIC5, CRYBA2, MUC6, TRNP1 and SEMG1) had increased mRNA expression in 13-30% of hypermutated and 0-3% of non-hypermutated colon cancers with Fischer exact p-value<0.01 (FIG. 10). Twenty-two of the thirty (73%) hypermutated colon cancers showed increased expression of at least one of the seven-gene panel. Seventeen of the twenty-two (77%) hypermutated colon cancers showing increased expression of at least one of the seven-gene panel also showed MLH1 silencing (FIG. 4B). Eleven of 51 genes showed frequent overexpression in CIMP-H and/or MLH1-silenced colon cancers including all 7 that showed frequent increased expression in hypermutated cancers (FIG. 11). Frequent increased expression of previous SSA/P markers (annexin A10—ANXA10 and claudin 1—CLDN1) in hypermutated and CIMP-H and/or MLH1 silenced colon cancers was not observed (21, 35) (FIGS. 9 and 11).

Microsatellite instability, CpG island methylation (CIMP), inactivation of MLH1 and BRAF mutations have been implicated as underlying events in the serrated pathway to colon cancer (14-18, 62). A recent study showed MLH1 silencing in a subgroup of hypermutated colon cancers that had increased BRAF and decreased APC and KRAS mutations. The authors concluded that MLH1 silencing occurred through a different pathway, suggestive of the serrated pathway (63). Not all SSA/Ps, however, have these changes, and it remains uncertain if they are requirements for the progression to cancer. A recent large serrated polyp study identified MLH1 methylation in 11% of SSA/Ps (64). As described herein, a new set of 51 genes are identified that are differently expressed in most SSA/Ps and sporadic MSI-high cancers in the TCGA cancer database. A smaller seven gene panel identified BRAF mutant, CIMP-H and MLH1 silenced colon cancers with both high sensitivity and specificity. The results described herein provide novel molecular markers for SSA/Ps that may play a role in the development of serrated colon cancers.

Example 5: Mutual Exclusivity and Co-Occurrence Analysis

Mutual exclusivity and co-occurrence of genomic alterations in each of the 51 signature genes disclosed herein and incidence of BRAF mutations was evaluated using the cBioPortal for Cancer Genomics. This analysis uses a previously published statistical method, Mutual Exclusivity Modules (MEMo), to identify genes that may be involved in the same cancer pathway (34). This method employs a "switching permutation" to derive a p-value for each gene combination. A log odds ratio was also determined to quantify how strongly an alteration found in Gene A is associated with an alteration found in Gene B.

Results.

Using the cBioPortal, concurrent genomic alterations (RNA expression and somatic mutation) in each of our 51-gene panel were evaluated and two genes from previous microarray studies (ANXA10 and CLDN1) with alterations in BRAF were also evaluated (21, 35). Thirteen of fifty-one signature genes with increased mRNA expression showed statistically significant associations with BRAF mutation in TCGA colon cancers both by Fisher exact test and log odds ratio (FIG. 12). Six of these genes (FSCN1, ZIC5, CRYBA2, MUC6, TRNP1 and SEMG1) were common to genes frequently overexpressed in hypermutated, CIMP-H and/or MLH1-silenced colon cancers. Mutual exclusivity and co-occurrence statistics are also shown for two previously developed SSA/P gene markers, annexin A10 (ANXA10) and claudin 1 (CLDN1) (FIG. 12). ZIC2 and CLDN1 did not show significant associations with BRAF mutation and ANXA10 showed a positive association by logs odds ratio but not the Fisher exact test.

Example 6: Sensitivity and Specificity of a Seven Gene Panel

The sensitivity and specificity of a seven-gene panel was evaluated in 182 TCGA colon cancer samples with gene expression, methylation and BRAF mutation data available. There were 31 MLH1 silenced, CIMP high and/or BRAF mutant samples out of 182 regarded as positive and the rest as negative. Cutoffs for each gene were set at 2 times the average expression of all samples. K-fold cross validation was used to get an estimate of sensitivity and specificity. In addition to individual expression, the panels of genes were also investigated.

The sensitivity and specificity of a SSA/P seven gene panel plus ANXA10 or CLDN1 were also assessed in identifying BRAF mutant, CIMP-H and/or MLH1 silenced colon cancers from the Cancer Genome Atlas (TCGA). Normalized RNA-Seq gene expression data for each gene was downloaded from the cBioPortal for Cancer Genomics as described herein.

Since it is well known that application of an algorithm to the data on which it was trained gives an overly optimistic estimate of performance, cross validation was carried out. Cross validation is designed to give a more accurate estimate of performance using training data sets only slightly smaller than the original data. Briefly K-fold cross-validation works as follows. The samples are partitioned into K complementary subsets of roughly equal size. Each "fold" consists of training the algorithm on a training data set formed from the union of K−1 of these subsets, and then validating on the remaining portion, called the testing data set. This procedure is repeated K times such a way that each sample in a testing data is set exactly once. For n-fold cross validation, each testing data set consists of a single sample. Thus, for the panels, the count of the number of genes above the 2-fold threshold was considered as a predictor.

PCR validation was performed on 4 of these genes FSCN1, ZIC5, SEMG1 and MUC6. mRNA expression for each gene was determined using commercially available TaqMan gene expression assays (Invitrogen) and a Applied Biosystems 7900HT real-time PCR instrument. 10 ul qPCR reactions were performed with forward and reverse primers, internal probe, master mix and 10-15 ng cDNA. cDNA was made from total RNA using the High Capacity RNA to cDNA kit (Invitrogen). A total of 73 samples were analyzed, 21 SSA/Ps, 12 HPs, 17 uninvolved and 23 control colon. Beta-actin was used a reference and control colon as the baseline for determining fold change using the AACT method. Statistical significance was determined by the non-parametric Mann Whitney U test.

Results.

Figure 8:
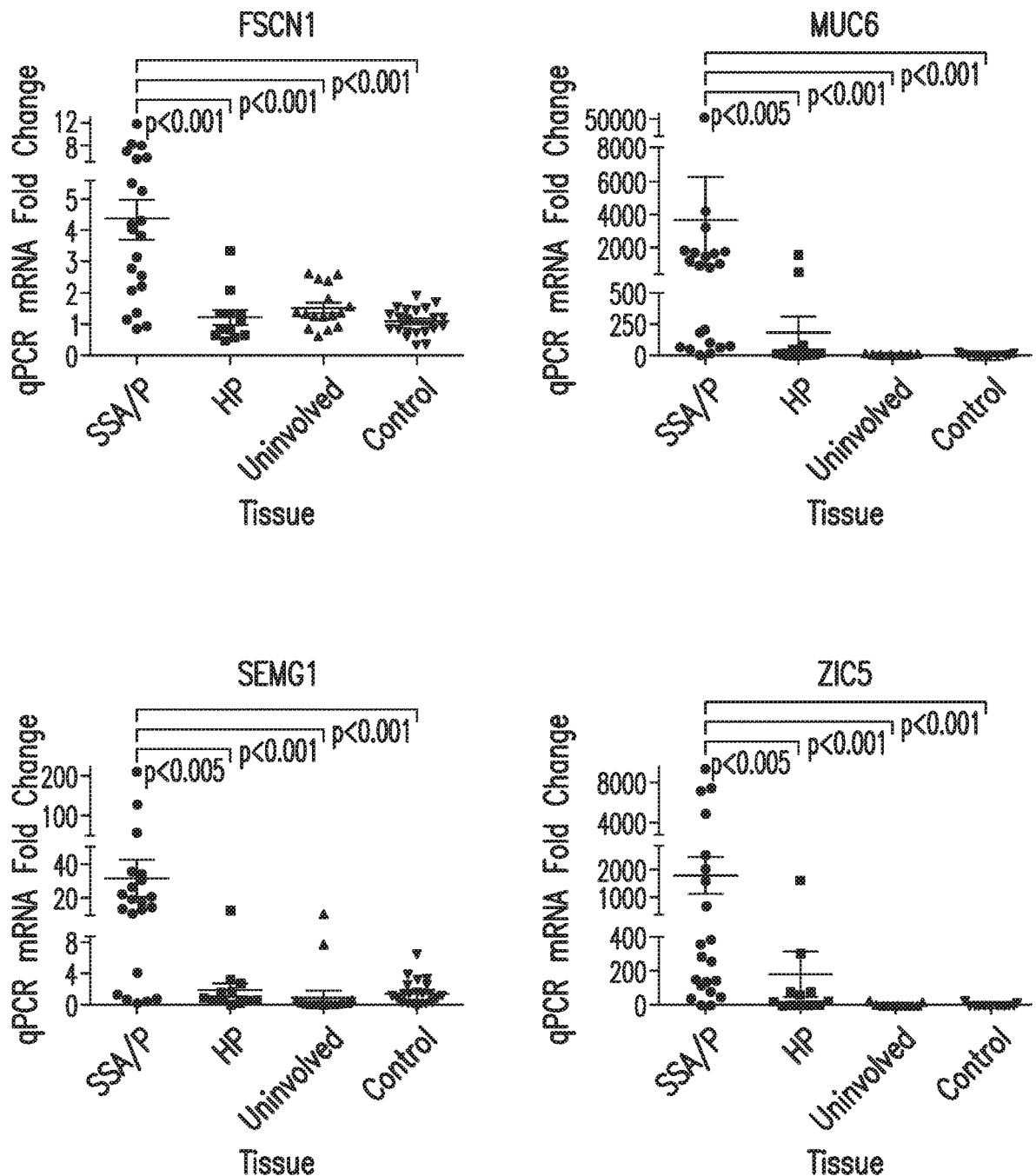
FIG. 8 shows mRNA expression of four SSA/P signature genes (FSCN1, MUC6, SEMG1 and ZIC5) in SSA/Ps, HPs, uninvolved colon and control colon by quantitative RT-PCR (qPCR).

Using a seven gene panel (FSCN1, ZIC2, ZIC5, CRYBA2, MUC6, TRNP1 and SEMG1) the sensitivity and specificity of each gene in identifying 31 BRAF mutant, CIMP-H and/or MLH1 silenced colon cancers out of 182 total colon cancers from the TCGA database were determined (FIG. 10A). The specificity of each gene in identifying this subset of cancers was high, between 85 and 99%. SSA/P RNA markers ANXA10 and CLDN1 showed similar specificity to our seven gene panel. In contrast, the sensitivity of each gene in identifying BRAF mutant, CIMP-H and/or MLH1 silenced colon cancers was more variable between genes (26-68%) with ZIC5 showing the highest sensitivity at 68%. The two previously identified RNA markers for SSA/Ps were lower with 19% and 6% sensitivity for ANXA10 and CLDN1, respectively. Using a seven-gene panel our sensitivity increased to 94% if at least one of the seven genes showed a two-fold increase in expression (FIG. 10B). Using ANXA10 or CLDN1 with our seven-gene panel the sensitivity was 97% and 94%, and the specificity was 72% and 63%, respectively (FIG. 13). qPCR validation was performed on 4 genes (FSCN1, ZIC5, SEMG1 and MUC6) and showed high expression in SSA/Ps consistent with RNA-seq data (FIG. 8).

The seven-gene panel (FSCN1, ZIC2, ZIC5, CRYBA2, MUC6, TRNP1 and SEMG1) described herein identified BRAF mutant, CIMP-H and MLH1 silenced colon cancers with high sensitivity and specificity. In comparison with other gene markers described for SSA/Ps (ANXA10 and CLDN1) the seven-gene panel showed increased sensitivity and similar specificity. This increase in sensitivity might be related to the use of RNA-Seq versus microarray technology. RNA-Seq provides a more quantitative analysis of transcript abundance and is not dependent on previously defined gene annotation. Also, the analysis of SSA/Ps from serrated polyposis (SPS) patients, known to have high colon cancer risk, may have further increased the ability to identify a gene signature more closely associated with sporadic colon cancer developing from the serrated pathway.

Some of the genes uniquely overexpressed in SSA/Ps relative to HPs participate in colon cancer progression. Increased expression of the transcriptional regulatory zinc finger proteins, ZIC2 and ZIC5, was found in both SSA/Ps and hypermutated colon cancers when compared to HPs and had negligible expression in the normal colonic mucosa. ZIC proteins play a role in regulating the sonic hedgehog and Wnt/B-catenin pathways (40, 41). ZIC2 has been associated with multiple cancers including brain, ovarian and cervical cancer (42, 43).

MUC6 is a gastric mucin gene shown to have increased expression in sessile serrated polyps when compared to hyperplastic polyps (44). Increased expression of MUC6 has also been documented in hypermethylated colon cancers suggesting its possible role in the serrated pathway (45). FSCN1 is an actin-binding protein frequently overexpressed in a variety of cancers including colon cancer and predicts poor prognosis (46). It was shown to be highly expressed in serrated colon cancers (47). Data lacks about the role of other genes SEMG1, TRNP1 and CRYBA2 noted in our panel in colon cancer. SEMG1 is a seminal vesical protein coding gene and has been studied as a biomarker for detection of prostate cancer (48). TMF-regulated nuclear protein (TRNP1) is a nuclear protein and plays a role in mammalian brain cortex development (49). CRYBA2 belongs to beta/gamma-crystallin family of genes and is found to be hypermethylated in CIMP-H neuroblastoma tumors (50). Three genes (FSCN1, TRNP1, ZIC2) of the seven-gene panel disclose herein were previously identified to be overexpressed in BRAF positive colon cancers in a European patient cohort (54). These genes were part of a 64-gene expression classifier for BRAF positive colon cancers with poor prognosis. Another study classifying colon cancers into four consensus molecular subtypes with subtype 1 (CMS1) consisting of microsatellite unstable, CIMP-H and BRAF positive tumors identified one of the seven-gene panel (ZIC2) disclosed herein as a marker of serrated cancers (55, 56). The results described herein compliments these findings and reinforces the importance of these genes in serrated colon cancers providing the first evidence that these mRNA changes occur early in the cancer process in pre-neoplastic serrated lesions (SSA/Ps).

REFERENCES

1. Department of Health and Human Services, Centers for Disease Control and Prevention, and National Cancer Institute; 2010
2. Burgess N G, Pellise M, Nanda K S, et al. Clinical and endoscopic predictors of cytological dysplasia or cancer in a prospective multicentre study of large sessile serrated adenomas/polyps. Gut. 2015 Mar. 2.
3. Lieberman D A, Weiss D G, Bond J H, et al. Use of colonoscopy to screen asymptomatic adults for colorectal cancer. Veterans Affairs Cooperative Study Group 380. N Engl J Med. 2000; 343:162-8
4. Kahi C J, Hewett D G, Norton D L, et al. Prevalence and variable detection of proximal colon serrated polyps during screening colonoscopy. Clin Gastroenterol Hepatol. 2011; 9:42-6.
5. Snover D C, Burt R W, Odze R D. Serrated Polyps of the colon and rectum and serrated polyposis Boxman, F T, Hruban, R H, Theise, N D, ed WHO Classification of Tumors of the Digestive System IARC, Lyon, 2010: 160-165.
6. Torlakovic E, Skovlund E, Snover D C, et al. Morphologic reappraisal of serrated colorectal polyps. Am J Surg Pathol. 2003; 27:65-81
7. Wong N A, Hunt L P, Novelli M R, et al. Observer agreement in the diagnosis of serrated polyps of the large bowel. Histopathology. 2009; 55:63-6.
8. Khalid O, Radaideh S, Cummings O W, et al. Reinterpretation of histology of proximal colon polyps called hyperplastic in 2001. World J Gastroenterol. 2009; 15:3767-70.
9. Jasperson K W, Kanth P, Kirchhoff A C, et al. Serrated polyposis: colonic phenotype, extracolonic features, and familial risk in a large cohort. Dis Colon Rectum. 2013 November; 56(11):1211-6.
10. Rashid A, Houlihan P S, Booker S, et al. Phenotypic and molecular characteristics of hyperplastic polyposis. Gastroenterology. 2000; 119:323-32.
11. Boparai K S, Mathus-Vliegen E M, Koornstra J J, et al. Increased colorectal cancer risk during follow-up in patients with hyperplastic polyposis syndrome: a multicentre cohort study. Gut. 2010; 59: 1094-100.
12. Holme O, Bretthauer M, Eide T J, et al. Long-term risk of colorectal cancer in individuals with serrated polyps. Gut. 2014 Nov. 16.
13. Mäkinen M. J. Colorectal serrated adenocarcinoma. Histopathology. 2007; 50:131-150.
14. O'Brien M J. Hyperplastic and serrated polyps of the colorectum. Gastroenterol Clin North Am. 2007; 36:947-968.
15. O'Brien M J1, Zhao Q, Yang S. Colorectal serrated pathway cancers and precursors. Histopathology. 2014 Sep. 29.
16. Iino H, Jass J R, Simms L A, et al. DNA microsatellite instability in hyperplastic polyps, serrated adenomas, and mixed polyps: a mild mutator pathway for colorectal cancer? J Clin Pathol. 1999; 52:5-9.
17. Guarinos C, Sánchez-Fortún C, Rodriguez-Soler M, et al. Clinical subtypes and molecular characteristics of serrated polyposis syndrome. Clin Gastroenterol Hepatol. 2013 June; 11(6):705-11
18. Samowitz W S, Albertsen H, Herrick J, et al. Evaluation of a large, population-based sample supports a CpG island methylator phenotype in colon cancer. Gastroenterology. 2005; 129:837-845
19. Samadder N J, Curtin K, Tuohy T M, et al. Characteristics of missed or interval colorectal cancer and patient survival: a population-based study. Gastroenterology. 2014 April; 146(4):950-60.
20. Richter J M, Pino M S, Austin T R, et al. Genetic mechanisms in interval colon cancers. Dig Dis Sci. 2014 September; 59(9):2255-63.
21. Gonzalo D H, Lai K K, Shadrach B, et al. Gene expression profiling of serrated polyps identifies annexin A10 as a marker of a sessile serrated adenoma/polyp. J Pathol. 2013 August; 230(4):420-9.
22. Caruso M, Moore J, Goodall G J, et al. Over-expression of cathepsin E and trefoil factor 1 in sessile serrated adenomas of the colorectum identified by gene expression analysis. Virchows Arch. 2009 March; 454(3):291-302.
23. Delker D A, McGettigan B M, Kanth P, et al. RNA sequencing of sessile serrated colon polyps identifies differentially expressed genes and immunohistochemical markers. PLoS One. 2014 Feb. 12; 9(2)
24. Lieberman D A, Rex D K, Winawer S J, et al. United States Multi-Society Task Force on Colorectal Cancer. Guidelines for colonoscopy surveillance after screening and polypectomy: a consensus update by the U S Multi-Society Task Force on Colorectal Cancer. Gastroenterology. 2012 September; 143(3):844-57.
25. Folkers M E, Delker D A, Maxwell C I, et al. ENCODE tiling array analysis identifies differentially expressed annotated and novel 5' capped RNAs in hepatitis C infected liver. PLoS One. 2011; Feb. 16; 6(2)
26. Papic N, Maxwell C I, Delker D A, et al. RNA-sequencing analysis of 5' capped RNAs identifies many new differentially expressed genes in acute hepatitis C virus infection. Viruses. 2012 April; 4(4):581-612.
27. Nix D A, Courdy S J, Boucher K M. Empirical methods for controlling false positives and estimating confidence in ChIP-Seq peaks. BMC Bioinformatics. 2008; 9:523. Epub 2008/12/09.
28. Anders S, Huber W. Differential expression analysis for sequence count data. Genome biology. 2010; 11(10): R106. Epub 2010/10/29.

29. Benjamini Y, Hochberg, Y. Controlling the false discovery rate: a practical and powerful approach to multiple testing. J Roy Statist Soc Ser B (Methodological). 1995; 57:289-300.
30. Love M I, Huber W, and Anders S. Moderated estimation of fold change and dispersion for RNA-Seq data with DESeq2. Genome Biology 2014, 15: 550
31. Comprehensive molecular characterization of human colon and rectal cancer. Cancer Genome Atlas Network. Nature. 2012 Jul. 18; 487(7407):330-7.
32. Gao J, Aksoy B A, Dogrusoz U, et al. Integrative analysis of complex cancer genomics and clinical profiles using the cBioPortal. Sci Signal. 2013 Apr. 2; 6(269):pl1.
33. Cerami E, Gao J, Dogrusoz U, et al. The cBio cancer genomics portal: an open platform for exploring multidimensional cancer genomics data. Cancer Discov. 2012 May; 2(5):401-4.
34. Ciriello, G., E. Cerami, et al. (2012). "Mutual exclusivity analysis identifies oncogenic network modules." Genome Res 22(2): 398-406.
35. Caruso M l, Fung K Y2, Moore J3, et al. Claudin-1 Expression Is Elevated in Colorectal Cancer Precursor Lesions Harboring the BRAF V600E Mutation. Transl Oncol. 2014 August; 7(4):456-63.
38. DiSario J A, Foutch P G, Mai H D, et al. Prevalence and malignant potential of colorectal polyps in asymptomatic, average-risk men. Am J Gastroenterol. 1991 August; 86(8):941-5.
39. Weston A P, Campbell D R. Diminutive colonic polyps: histopathology, spatial distribution, concomitant significant lesions, and treatment complications. Am J Gastroenterol. 1995 January; 90(1):24-8.
40. Merzdorf C S. Emerging roles for zic genes in early development. Dev Dyn. 2007 April; 236(4):922-40.
41. Sanek N A, Taylor A A, Nyholm M K, et al. Zebrafish zic2a patterns the forebrain through modulation of Hedgehog-activated gene expression. Development. 2009 November; 136(22):3791-800.
42. Marchini S, Poynor E, Barakat R R, et al. The zinc finger gene ZIC2 has features of an oncogene and its overexpression correlates strongly with the clinical course of epithelial ovarian cancer. Clin Cancer Res. 2012 Aug. 15; 18(16):4313-24.
43. Chan D W, Liu V W, Leung L Y, et al. Zic2 synergistically enhances Hedgehog signalling through nuclear retention of Gli1 in cervical cancer cells. J Pathol. 2011 December; 225(4):525-34.
44. Owens S R, Chiosea S I, Kuan S F. Selective expression of gastric mucin MUC6 in colonic sessile serrated adenoma but not in hyperplastic polyp aids in morphological diagnosis of serrated polyps. Mod Pathol. 2008 June; 21(6):660-9.
45. Walsh M D, Clendenning M, Williamson E et al. Expression of MUC2, MUCSAC, MUCSB, and MUC6 mucins in colorectal cancers and their association with the CpG island methylator phenotype. Mod Pathol. 2013 December; 26(12):1642-56
46. Ma Y, Machesky L M. Fascinl in carcinomas: Its regulation and prognostic value. Int J Cancer. 2014 Oct. 10.
47. Conesa-Zamora P1, Garcia-Solano J, Garcia-Garcia F, et al. Int J Cancer. 2013 Jan. 15; 132(2):297-307. Expression profiling shows differential molecular pathways and provides potential new diagnostic biomarkers for colorectal serrated adenocarcinoma.
48. Neuhaus J, Schiffer E, von Wilcke P, et al. Seminal plasma as a source of prostate cancer peptide biomarker candidates for detection of indolent and advanced disease. PLoS One. 2013 Jun. 24; 8(6):e67514.
49. Stahl R1, Walcher T, De Juan Romero C, et al. Cell. 2013 Apr. 25; 153(3):535-49.Tmp1 regulates expansion and folding of the mammalian cerebral cortex by control of radial glial fate.
50. Abe M, Watanabe N, McDonell N, et al. Oncology. 2008; 74(1-2):50-60. Identification of genes targeted by CpG island methylator phenotype in neuroblastomas, and their possible integrative involvement in poor prognosis.
51. Sun Y, Shen S, Liu X, et al. MiR-429 inhibits cells growth and invasion and regulates EMT-related marker genes by targeting Onecut2 in colorectal carcinoma. Mol Cell Biochem. 2014 May; 390(1-2):19-30.
52. Paz M F, Wei S, Cigudosa J C, et al. Genetic unmasking of epigenetically silenced tumor suppressor genes in colon cancer cells deficient in DNA methyltransferases. Hum Mol Genet. 2003 Sep. 1; 12(17):2209-19.
53. Kang S K, Chae Y K, Woo J, et al. Role of human aquaporin 5 in colorectal carcinogenesis. Am J Pathol. 2008 August; 173(2):518-25.
54. Popovici V, Budinska E, Tejpar S, et al. Identification of a poor-prognosis BRAF-mutant-like population of patients with colon cancer. J Clin Oncol. 2012 Apr. 20; 30(12):1288-95.
55. Guinney J, Dienstmann R, Wang X, et al. The consensus molecular subtypes of colorectal cancer. Nat Med. 2015 November; 21(11):1350-6.
56. De Sousa E Melo F, Wang X, Jansen M, et al. Poor-prognosis colon cancer is defined by a molecularly distinct subtype and develops from serrated precursor lesions. Nat Med. 2013 May; 19(5):614-8.
57. Hawthorn L, Lan L, Mojica W. Evidence for field effect cancerization in colorectal cancer. Genomics. 2014 February-March; 103(2-3):211-21.
58. Lochhead P, Chan A T, Nishihara R, et al. Etiologic field effect: reappraisal of the field effect concept in cancer predisposition and progression. Mod Pathol. 2015 January; 28(1):14-29.
59. Chen L C, Hao C Y, Chiu Y S, et al. Alteration of gene expression in normal-appearing colon mucosa of APC (min) mice and human cancer patients. Cancer Res. 2004 May 15; 64(10):3694-700.
60. Luo Y, Yu M, Grady W M. Field cancerization in the colon: a role for aberrant DNA methylation? Gastroenterol Rep (Oxf). 2014 February; 2(1):16-20.
61. Damania D, Roy H K, Subramanian H, et al. Nanocytology of rectal colonocytes to assess risk of colon cancer based on field cancerization. Cancer Res. 2012 Jun. 1; 72(11):2720-7.
62. Huang C S, Farraye F A, Yang S, et al. The clinical significance of serrated polyps. Am J Gastroenterol. 2011 February; 106(2):229-40
63. Donehower L A, Creighton C J, Schultz N, et al. MLH1-silenced and non-silenced subgroups of hypermutated colorectal carcinomas have distinct mutational landscapes. J Pathol. 2013 January; 229(1):99-110.
64. Burnett-Hartman A N, Newcomb P A, Potter J D, et al. Genomic aberrations occurring in subsets of serrated colorectal lesions but not conventional adenomas. Cancer Res. 2013 May 1; 73(9):2863-72.

What is claimed is:

1. A gene expression panel for assessing risk of developing colon cancer in a human subject, comprising labeled primers or probes that specifically hybridize to FSCN1, ZIC2, ZIC5, CRYBA2, MUC6, TRNP1 and SEMG1 in a sample, wherein the label is attached to the primers or probes, and wherein gene expression panel does not comprise labeled primers or probes that specifically hybridize to CLDN1 or ANAX10 in a sample.

2. The gene expression panel of claim 1, wherein the labeled primers are nucleic acids.

* * * * *